United States Patent
Yamamoto et al.

(10) Patent No.: US 11,583,257 B2
(45) Date of Patent: Feb. 21, 2023

(54) ULTRASOUND DIAGNOSTIC APPARATUS AND OPERATION METHOD OF ULTRASOUND DIAGNOSTIC APPARATUS

(71) Applicant: FUJIFILM Corporation, Tokyo (JP)

(72) Inventors: Katsuya Yamamoto, Ashigarakami-gun (JP); Yasuhiko Morimoto, Ashigarakami-gun (JP); Satoru Okada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 875 days.

(21) Appl. No.: 16/428,687

(22) Filed: May 31, 2019

(65) Prior Publication Data

US 2020/0000437 A1    Jan. 2, 2020

(30) Foreign Application Priority Data

Jun. 29, 2018  (JP) .............................. JP2018-124170

(51) Int. Cl.
  *A61B 8/00*   (2006.01)
  *A61B 8/12*   (2006.01)
  (Continued)

(52) U.S. Cl.
  CPC .................. *A61B 8/54* (2013.01); *A61B 8/12* (2013.01); *A61B 8/4488* (2013.01); *A61B 8/463* (2013.01);
  (Continued)

(58) Field of Classification Search
  CPC ........... A61B 8/54; A61B 8/12; A61B 8/4488; A61B 8/463; A61B 8/465; A61B 8/5207;
  (Continued)

(56) References Cited

U.S. PATENT DOCUMENTS 5,335,662 A * 8/1994 Kimura .................... H04N 7/18
                                                        600/459
6,636,254 B1 * 10/2003 Onishi ..................... G06T 3/60
                                                        348/65
(Continued)

FOREIGN PATENT DOCUMENTS

JP    2002-368301 A    12/2002
JP    2009-233247 A    10/2009
(Continued)

OTHER PUBLICATIONS

European Communication pursuant to Article 94(3) EPC for European Application No. 19175942.2, dated Mar. 26, 2021.
(Continued)

*Primary Examiner* — Baisakhi Roy
(74) *Attorney, Agent, or Firm* — Birch, Stewart, Kolasch & Birch, LLP

(57) ABSTRACT

In an ultrasound diagnostic apparatus and an operation method of the ultrasound diagnostic apparatus of the invention, a control circuit performs polarization processing on a plurality of ultrasound transducers in a non-diagnosis period, during which transmission of ultrasound waves and reception of reflected waves for performing ultrasound diagnosis are not performed, in a case where the cumulative driving time of the plurality of ultrasound transducers for performing the ultrasound diagnosis becomes equal to or longer than a specified time. A transmission circuit generates a first transmission signal having a driving voltage for performing ultrasound diagnosis using a pulse generation circuit in the case of performing the ultrasound diagnosis, and generates a second transmission signal having a polarization voltage for performing polarization processing using the same pulse generation circuit as in the case of generating
(Continued)

the first transmission signal in the case of performing the polarization processing.

20 Claims, 15 Drawing Sheets

(51) Int. Cl.
    *A61B 8/08*     (2006.01)
    *G01S 7/53*     (2006.01)
    *G01S 15/89*     (2006.01)
    *G01S 15/02*     (2006.01)
    *G01S 7/56*     (2006.01)
    *G01S 15/86*     (2020.01)

(52) U.S. Cl.
    CPC ............ *A61B 8/465* (2013.01); *A61B 8/5207* (2013.01); *A61B 8/5261* (2013.01); *A61B 8/5292* (2013.01); *G01S 7/53* (2013.01); *G01S 7/56* (2013.01); *G01S 15/86* (2020.01); *G01S 15/89* (2013.01)

(58) Field of Classification Search
    CPC ....... A61B 8/5261; A61B 8/5292; G01S 7/56; G01S 7/53; G01S 15/89; G01S 15/025
    See application file for complete search history.

(56) References Cited

U.S. PATENT DOCUMENTS

| | | | |
|---|---|---|---|
| 2004/0260181 A1 | 12/2004 | Makita et al. | |
| 2008/0033298 A1 | 2/2008 | Habu et al. | |
| 2009/0287086 A1* | 11/2009 | Hyuga | B06B 1/0607 600/459 |
| 2010/0053213 A1* | 3/2010 | Ishida | G16H 15/00 345/660 |
| 2010/0079586 A1* | 4/2010 | Abe | A61B 8/12 348/E5.057 |
| 2010/0168576 A1* | 7/2010 | Poland | G01S 7/5208 600/443 |
| 2012/0319529 A1 | 12/2012 | Nakazawa et al. | |
| 2012/0323514 A1* | 12/2012 | Nakazawa | H01L 41/257 29/25.35 |
| 2014/0066779 A1* | 3/2014 | Nakanishi | A61B 8/4444 600/459 |
| 2014/0257109 A1* | 9/2014 | Nishikubo | H01L 41/337 29/25.35 |
| 2017/0119349 A1* | 5/2017 | Miyazawa | A61B 8/4494 |
| 2017/0143310 A1* | 5/2017 | Funakubo | A61B 8/465 |
| 2017/0290571 A1* | 10/2017 | Funakubo | A61B 8/5223 |
| 2019/0343492 A1* | 11/2019 | Miyazawa | B06B 1/0622 |
| 2020/0000438 A1* | 1/2020 | Yamamoto | A61B 8/546 |
| 2021/0298714 A1* | 9/2021 | Van Der Horst | A61B 8/12 |

FOREIGN PATENT DOCUMENTS

| | | |
|---|---|---|
| JP | 2012-139460 A | 7/2012 |
| JP | 2013-4645 A | 1/2013 |
| JP | 2013-5137 A | 1/2013 |
| JP | 2013-168573 A | 8/2013 |
| JP | 2015-62621 A | 4/2015 |
| JP | 6158017 B2 | 7/2017 |
| JP | 2017-143353 A | 8/2017 |

OTHER PUBLICATIONS

Extended European Search Report for corresponding European Application No. 19175942.2, dated Oct. 25, 2019.
Japanese Office Action for Japanese Application No. 2018-124170, dated Jun. 15, 2021, with English translation.
Japanese Office Action dated Dec. 13, 2022 for Application No. 2021-210960 with an English translation.

* cited by examiner

FIG. 10
FIRST DISPLAY MODE
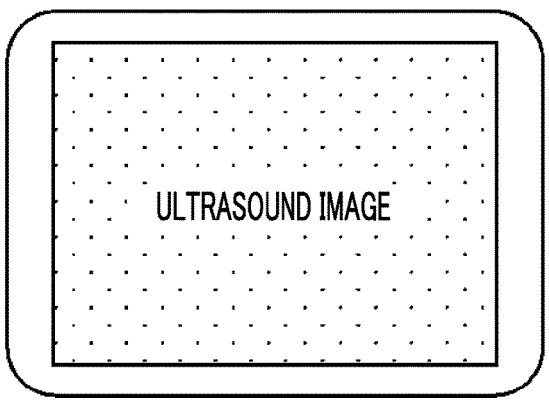
SECOND DISPLAY MODE
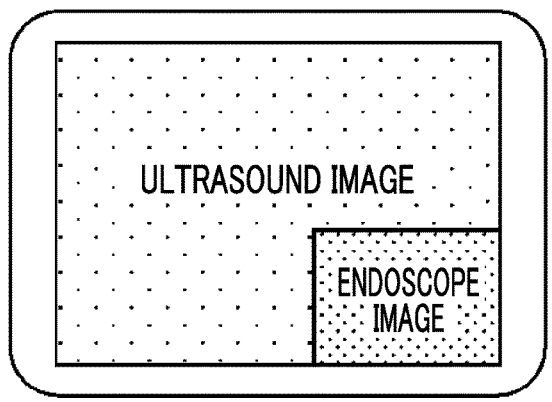
THIRD DISPLAY MODE
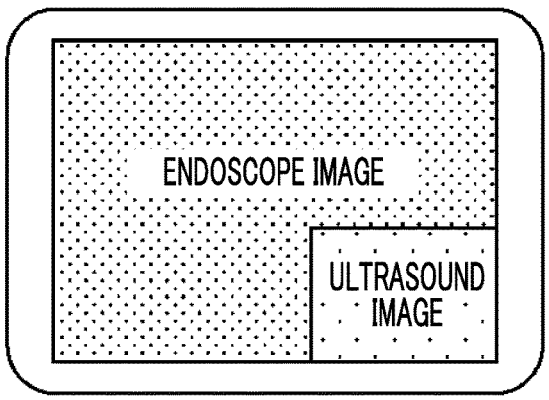
FOURTH DISPLAY MODE
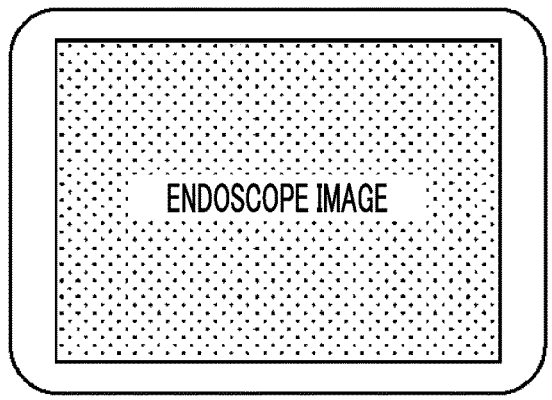

ULTRASOUND DIAGNOSTIC APPARATUS AND OPERATION METHOD OF ULTRASOUND DIAGNOSTIC APPARATUS

CROSS-REFERENCE TO RELATED APPLICATIONS

The present application claims priority under 35 U.S.C. § 119 to Japanese Patent Application No. 2018-124170, filed on Jun. 29, 2018. Each of the above application(s) is hereby expressly incorporated by reference, in its entirety, into the present application.

BACKGROUND OF THE INVENTION

1. Field of the Invention

The present invention relates to an ultrasound diagnostic apparatus, which performs polarization processing on a plurality of ultrasound transducers that an ultrasound endoscope comprises, and an operation method of an ultrasound diagnostic apparatus.

2. Description of the Related Art

An ultrasound diagnostic apparatus that acquires an ultrasound image of the inside of a subject by transmitting and receiving ultrasound waves by driving a plurality of ultrasound transducers inside the subject is already known. In the ultrasound diagnostic apparatus, the plurality of ultrasound transducers are, for example, single crystal transducers that are piezoelectric elements, and are usually used in a polarized state. The ultrasound transducer that is a single crystal transducer can receive ultrasound waves with high sensitivity, but a depolarization phenomenon in which the degree of polarization decreases as the driving time increases may occur. In a case where a depolarization phenomenon occurs, the reception sensitivity of the ultrasound transducer decreases, which may affect the image quality of the ultrasound image.

In particular, in the case of transmitting and receiving ultrasound waves by driving each ultrasound transducer inside the subject, since it is necessary to set the frequency of the ultrasound wave to a high frequency band of 7 MHz to 8 MHz level, a transducer having a relatively small thickness is used. However, as the thickness of the transducer decreases, the risk of occurrence of a depolarization phenomenon increases.

For this reason, techniques for countermeasures against depolarization in the ultrasound diagnostic apparatus have been developed so far. For example, an ultrasound diagnostic apparatus (referred to as a "piezoelectric sensor apparatus" in JP2013-005137A) described in JP2013-005137A has a piezoelectric element having a piezoelectric body and a pair of electrodes interposing the piezoelectric body therebetween, a detection circuit for performing detection processing for detecting a detection signal output from the piezoelectric element, and a polarization processing circuit for performing polarization processing by applying a polarization voltage to the piezoelectric element. In the ultrasound diagnostic apparatus described in JP2013-005137A having such a configuration, for example, polarization processing is performed at a timing at which the electric power is supplied, a timing at which a request signal for performing detection processing is input (each reception timing), or a timing at which a predetermined standby transition time has passed after the end of detection processing, and the polarization processing is ended in a case where it is determined that the polarization processing has ended by counting the processing time with a timer. Therefore, even in a case where a depolarization phenomenon occurs in the piezoelectric element, the piezoelectric element can be polarized again. As a result, it is possible to maintain the reception sensitivity of the piezoelectric element.

As another example, an ultrasound diagnostic apparatus (referred to as an "ultrasound sensor" in JP2017-143353A) described in JP2017-143353A has a piezoelectric element and a driving circuit for driving the piezoelectric element. The driving circuit drives the piezoelectric element with a driving waveform having first to sixth steps. The first step is a step of maintaining the polarization of the piezoelectric element with a first potential $V1$. The second step is a step of transmitting an ultrasound wave to the piezoelectric element after the first step. The third step is a step of causing the piezoelectric element to stand by at a second potential $V2$ after the second step. The fourth step is a step of increasing the second potential $V2$ to a third potential $V3$ after the third step. The fifth step is a step of maintaining the third potential $V3$ while the piezoelectric element receives an ultrasound wave after the fourth step. The sixth step is a step of returning the third potential $V3$ to the first potential $V1$ after the fifth step. In the ultrasound diagnostic apparatus described in JP2017-143353A having such a configuration, it is possible to drive the piezoelectric element while maintaining the polarization of the piezoelectric element by driving the piezoelectric element with the driving waveform having the first to sixth steps described above.

The ultrasound diagnostic apparatus described in JP2012-139460A has an ultrasound probe including a piezoelectric element, a storage unit that stores a threshold value of a physical quantity that changes with the degree of depolarization of the piezoelectric element, a recording unit that records the cumulative use time of the ultrasound probe, a detection unit that detects a physical quantity in the ultrasound probe, and a high voltage application unit that applies a high voltage for repolarizing the piezoelectric element to an electrode pair of the piezoelectric element. In the ultrasound diagnostic apparatus described in JP2012-139460A having such a configuration, a physical quantity (for example, a voltage value of a reception signal) is detected in a case where the cumulative use time of the ultrasound probe reaches a predetermined time, and a high voltage is applied to the electrode pair to perform repolarization processing in a case where it is determined that the detection result of the physical quantity is equal to or less than the threshold value. In this manner, it is possible to cope with degradation of the polarization characteristic of the piezoelectric element of the ultrasound probe at an appropriate timing.

An ultrasound diagnostic apparatus (referred to as an "ultrasound apparatus" in JP6158017B) described in JP6158017B has an ultrasound transducer that transmits and receives ultrasound waves to and from a subject and a controller that performs control to apply a polarization voltage to the ultrasound transducer. In the ultrasound diagnostic apparatus described in JP6158017B having such a configuration, a polarization voltage set to be a voltage having a magnitude used to transmit ultrasound waves for acquiring an ultrasound image is applied to the ultrasound transducer in a state in which the ultrasound transducer is excited and heated. By heating the ultrasound transducer, the polarization voltage can be made lower than that at the room temperature. Therefore, it is possible to perform repolarization processing using a circuit that performs transmission beam forming.

SUMMARY OF THE INVENTION

As described above, in the ultrasound diagnostic apparatus described in each of JP2013-005137A, JP2017-143353A, JP2012-139460A, and P6158017B, it is possible to restore or maintain the polarization of the piezoelectric element.

However, as in the ultrasound diagnostic apparatus described in JP2013-005137A, providing a dedicated circuit for performing repolarization, a depolarization detection mechanism, and the like is a large hardware change factor. Accordingly, it is very difficult to mount those described above in the existing system. The same applies to a case where it is necessary to provide a high voltage application unit that applies a high voltage for repolarizing a piezoelectric element to an electrode pair of the piezoelectric element as in the ultrasound diagnostic apparatus described in JP2012-139460A.

On the other hand, JP6158017B describes the ultrasound diagnostic apparatus that performs repolarization processing using a circuit that performs transmission beam forming. However, in the ultrasound diagnostic apparatus described in JP6158017B, it is necessary to output a DC waveform for applying a polarization voltage to the ultrasound transducer in order to perform repolarization processing in addition to pulse waves for exciting the ultrasound transducer to transmit ultrasound waves in order to perform transmission beam forming. Therefore, since the pulse wave and the DC waveform are output in the same circuit, the circuit size becomes large. This may cause an increase in cost.

In the ultrasound diagnostic apparatus described in JP2017-143353A, in order to maintain polarization, the pulse length of the driving waveform is increased by inserting a DC component into each driving waveform. Accordingly, the frame rate may be reduced to affect the image quality of the ultrasound image.

It is an object of the invention to provide an ultrasound diagnostic apparatus and an operation method of an ultrasound diagnostic apparatus capable of performing polarization processing using an existing circuit without causing a cost increase and without affecting the image quality of an ultrasound image.

In order to achieve the aforementioned object, the invention provides an ultrasound diagnostic apparatus acquiring an ultrasound image and an endoscope image. The ultrasound diagnostic apparatus comprises: an ultrasound endoscope comprising an ultrasound observation portion that transmits ultrasound waves using an ultrasound transducer array in which a plurality of ultrasound transducers are arranged, receives reflected waves of the ultrasound waves, and outputs a reception signal; and an ultrasound processor apparatus that generates the ultrasound image by converting the reception signal into an image. The ultrasound processor apparatus comprises: a control circuit that performs polarization processing on the plurality of ultrasound transducers in a non-diagnosis period, during which transmission of the ultrasound waves and reception of the reflected waves for performing ultrasound diagnosis are not performed, in a case where a cumulative driving time of the plurality of ultrasound transducers for performing the ultrasound diagnosis becomes equal to or longer than a specified time; and a transmission circuit that generates a transmission signal for driving the plurality of ultrasound transducers to generate the ultrasound waves using a pulse generation circuit and supplies the transmission signal to the plurality of ultrasound transducers under control of the control circuit. The transmission circuit generates a first transmission signal having a driving voltage for performing the ultrasound diagnosis using the pulse generation circuit in a case of performing the ultrasound diagnosis, and generates a second transmission signal having a polarization voltage for performing the polarization processing using the same pulse generation circuit as in the case of generating the first transmission signal in a case of performing the polarization processing. Reception signals of the plurality of ultrasound transducers in a frequency band of a first ultrasound wave generated by the first transmission signal and reception signals of the plurality of ultrasound transducers in a frequency band of a main lobe of a second ultrasound wave generated by the second transmission signal have different band characteristics.

Here, it is preferable that band characteristics of the reception signals of the plurality of ultrasound transducers in the frequency band of the first ultrasound wave generated by the first transmission signal and band characteristics of the reception signals of the plurality of ultrasound transducers in the frequency band of the main lobe of the second ultrasound wave generated by the second transmission signal do not overlap at a level of −20 dB or more.

It is preferable that an operation mode includes a first mode in which the polarization processing is not performed during the non-diagnosis period and a second mode in which the polarization processing is performed during the non-diagnosis period. It is preferable that the control circuit shifts the operation mode from the first mode to the second mode in a case where the cumulative driving time becomes equal to or longer than the specified time in the first mode and shifts the operation mode from the second mode to the first mode in a case where a difference obtained by subtracting the cumulative driving time from a cumulative processing time of the plurality of ultrasound transducers for performing the polarization processing becomes equal to or greater than a threshold value in the second mode.

It is preferable that the control circuit performs the polarization processing in a case of a freeze mode in which an image of one frame of the ultrasound image is displayed.

It is preferable that the control circuit performs the polarization processing in a case where a screen for setting a control parameter of the ultrasound diagnostic apparatus is displayed.

It is preferable that the control circuit performs the polarization processing in a case where a screen for inputting information of a patient to be subjected to the ultrasound diagnosis is displayed.

It is preferable that the control circuit performs the polarization processing in a case where a screen for designating a part to be subjected to the ultrasound diagnosis is displayed.

It is preferable that the control circuit performs the polarization processing in a case where a screen for displaying an ultrasound image generated in a past is displayed.

It is preferable that the control circuit performs the polarization processing in a case where only the endoscope image is displayed.

It is preferable that the ultrasound processor apparatus further comprises a notification circuit that notifies a user that the polarization processing is being performed. It is preferable that the control circuit controls the notification circuit to notify the user that the polarization processing is being performed in a case where the ultrasound image is displayed so as to be smaller than the endoscope image by picture in picture and sets an operation mode to a freeze mode in which an image of one frame of the ultrasound image is displayed to perform the polarization processing.

In addition, the invention provides an operation method of an ultrasound diagnostic apparatus acquiring an ultrasound image and an endoscope image. The operation method of an ultrasound diagnostic apparatus comprises: a step in which an ultrasound observation portion that an ultrasound endoscope of the ultrasound diagnostic apparatus comprises transmits ultrasound waves using an ultrasound transducer array in which a plurality of ultrasound transducers are arranged, receives reflected waves of the ultrasound waves, and outputs a reception signal; and a step in which an ultrasound processor apparatus of the ultrasound diagnostic apparatus generates the ultrasound image by converting the reception signal into an image. The step of generating the ultrasound image includes: a step in which a control circuit of the ultrasound processor apparatus performs polarization processing on the plurality of ultrasound transducers in a non-diagnosis period, during which transmission of the ultrasound waves and reception of the reflected waves for performing ultrasound diagnosis are not performed, in a case where a cumulative driving time of the plurality of ultrasound transducers for performing the ultrasound diagnosis becomes equal to or longer than a specified time; and a step in which a transmission circuit of the ultrasound processor apparatus generates a transmission signal for driving the plurality of ultrasound transducers to generate the ultrasound waves using a pulse generation circuit and supplies the transmission signal to the plurality of ultrasound transducers under control of the control circuit. The step of generating the transmission signal includes: a step of generating a first transmission signal having a driving voltage for performing the ultrasound diagnosis using the pulse generation circuit in a case of performing the ultrasound diagnosis; and a step of generating a second transmission signal having a polarization voltage for performing the polarization processing using the same pulse generation circuit as in the case of generating the first transmission signal in a case of performing the polarization processing. Reception signals of the plurality of ultrasound transducers in a frequency band of a first ultrasound wave generated by the first transmission signal and reception signals of the plurality of ultrasound transducers in a frequency band of a main lobe of a second ultrasound wave generated by the second transmission signal have different band characteristics.

Here, it is preferable that band characteristics of the reception signals of the plurality of ultrasound transducers in the frequency band of the first ultrasound wave generated by the first transmission signal and band characteristics of the reception signals of the plurality of ultrasound transducers in the frequency band of the main lobe of the second ultrasound wave generated by the second transmission signal do not overlap at a level of −20 dB or more.

It is preferable that an operation mode includes a first mode in which the polarization processing is not performed during the non-diagnosis period and a second mode in which the polarization processing is performed during the non-diagnosis period. It is preferable that, in the step of performing the polarization processing, the operation mode is shifted from the first mode to the second mode in a case where the cumulative driving time becomes equal to or longer than the specified time in the first mode, and the operation mode is shifted from the second mode to the first mode in a case where a difference obtained by subtracting the cumulative driving time from a cumulative processing time of the plurality of ultrasound transducers for performing the polarization processing becomes equal to or greater than a threshold value in the second mode.

In the invention, the polarization processing is performed using the existing pulse generation circuit. In the ultrasound diagnostic apparatus, the second transmission signal in the case of performing polarization processing is a pulse wave, and the pulse generation circuit does not need to output a DC waveform. Therefore, it is possible to perform the polarization processing without significantly changing the existing circuit and accordingly without increasing the cost.

In addition, since the polarization processing is performed during the non-diagnosis period, the frame rate is not reduced. Therefore, without reducing the image quality of the ultrasound image, the reception sensitivities of the plurality of ultrasound transducers can always be kept satisfactory. As a result, a high-quality ultrasound image can always be acquired.

BRIEF DESCRIPTION OF THE DRAWINGS

FIG. 10 is a conceptual diagram of an example showing display modes.

DESCRIPTION OF THE PREFERRED EMBODIMENTS

An ultrasound diagnostic apparatus according to an embodiment (the present embodiment) of the invention will be described in detail below with reference to preferred embodiments shown in the accompanying diagrams.

The present embodiment is a representative embodiment of the invention, but is merely an example and does not limit the invention.

In addition, in this specification, the numerical range expressed by using "~" means a range including numerical values described before and after "~" as a lower limit and an upper limit.

<<Outline of Ultrasound Diagnostic Apparatus>>

Figure 1:
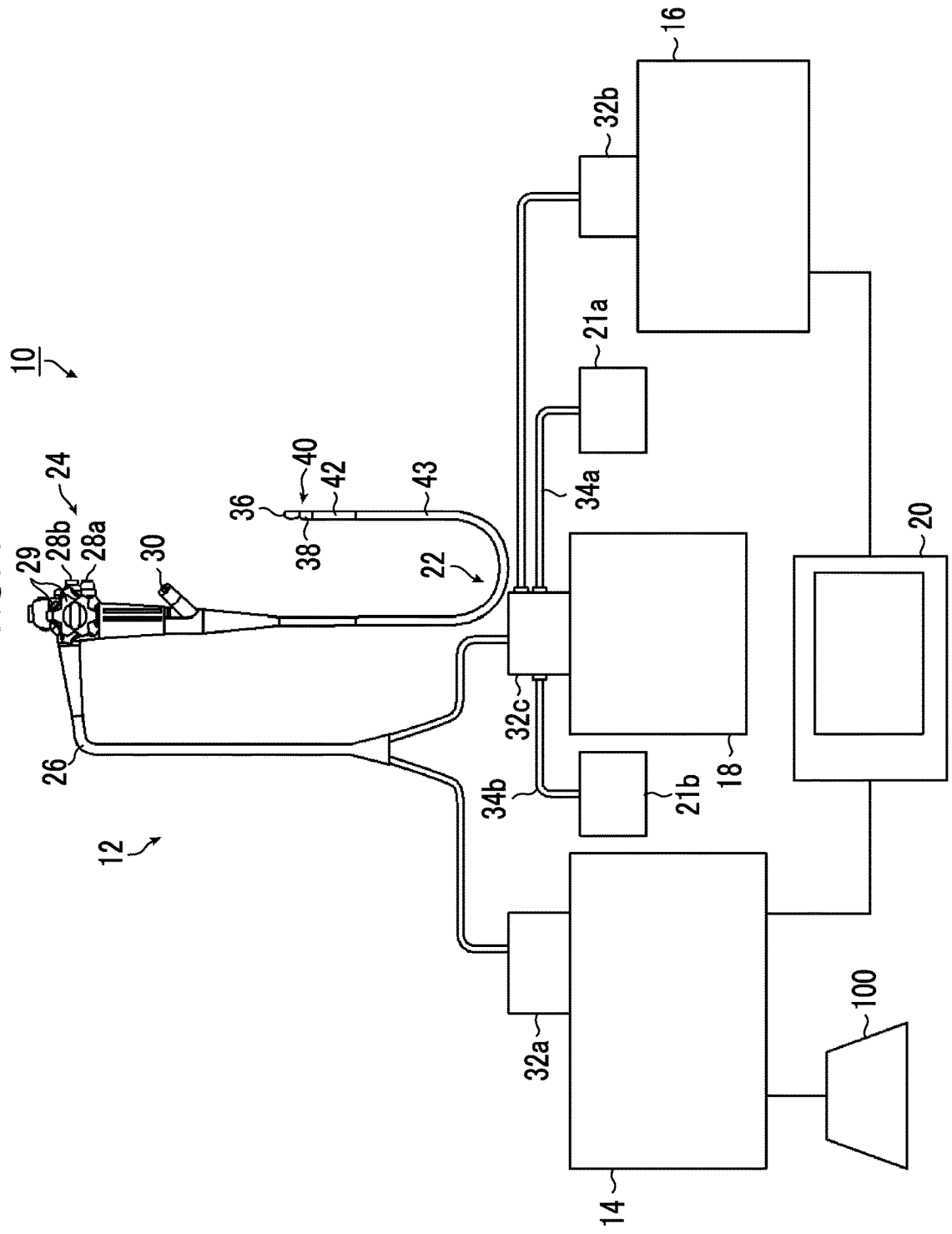
FIG. 1 is a diagram showing the schematic configuration of an ultrasound diagnostic apparatus according to an embodiment of the invention.

The outline of an ultrasound diagnostic apparatus 10 according to the present embodiment will be described with reference to FIG. 1. FIG. 1 is a diagram showing the schematic configuration of ultrasound diagnostic apparatus 10.

The ultrasound diagnostic apparatus 10 is used to observe (hereinafter, also referred to as ultrasound diagnosis) the state of an observation target part in a body of a patient, who is a subject, using ultrasound waves. Here, the observation target part is a part that is difficult to examine from the body surface side of the patient, for example, a gallbladder or a pancreas. By using the ultrasound diagnostic apparatus 10, it is possible to perform ultrasound diagnosis of the state of the observation target part and the presence or absence of an abnormality through gastrointestinal tracts such as esophagus, stomach, duodenum, small intestine, and large intestine which are body cavities of the patient.

The ultrasound diagnostic apparatus 10 acquires an ultrasound image and an endoscope image, and as shown in FIG. 1, has an ultrasound endoscope 12, an ultrasound processor apparatus 14, an endoscope processor apparatus 16, a light source device 18, a monitor 20, a water supply tank 21a, a suction pump 21b, and a console 100.

Figure 2:
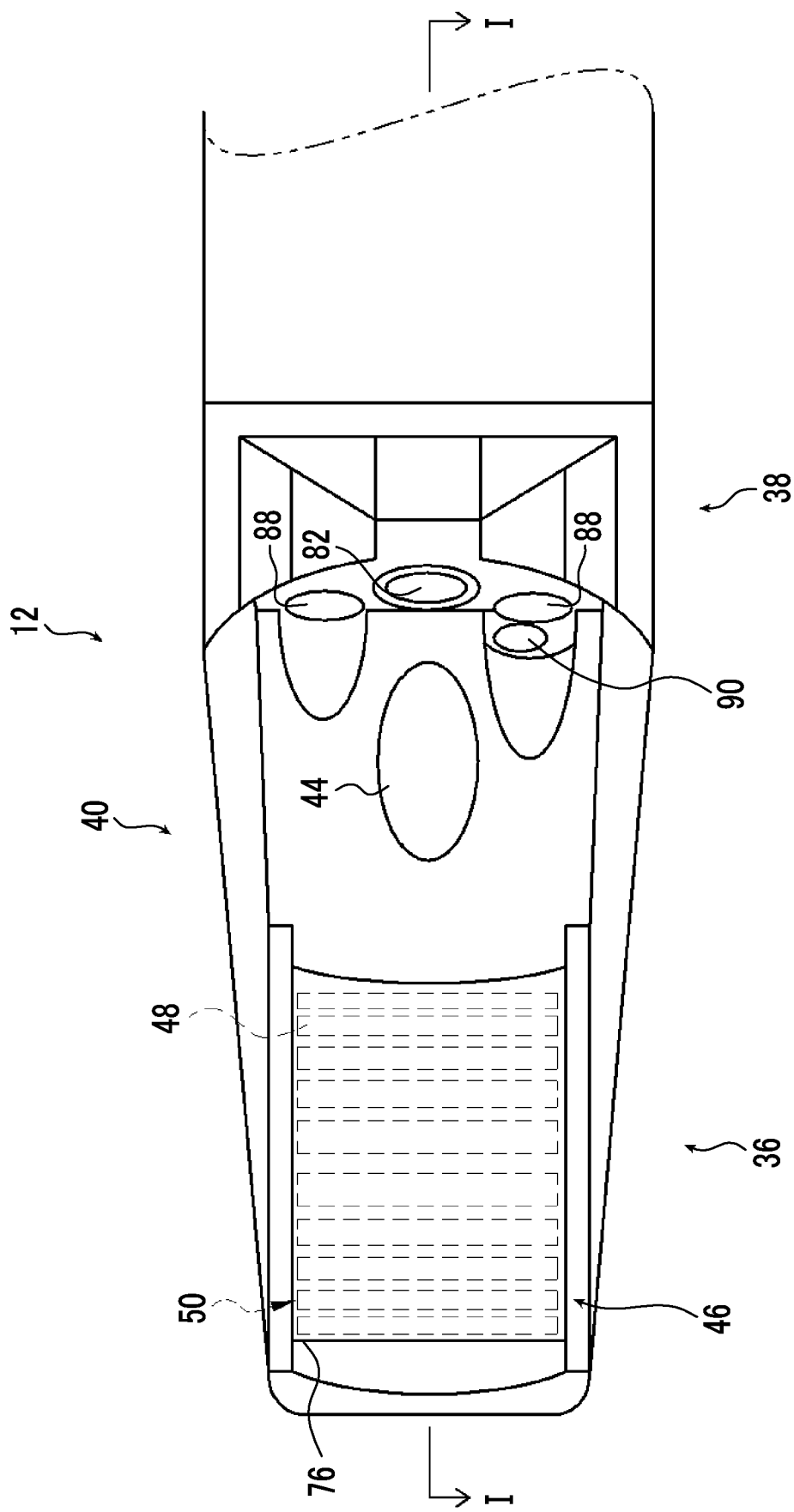
FIG. 2 is a plan view showing a distal end portion of an insertion part of an ultrasound endoscope and its periphery.
Figure 3:
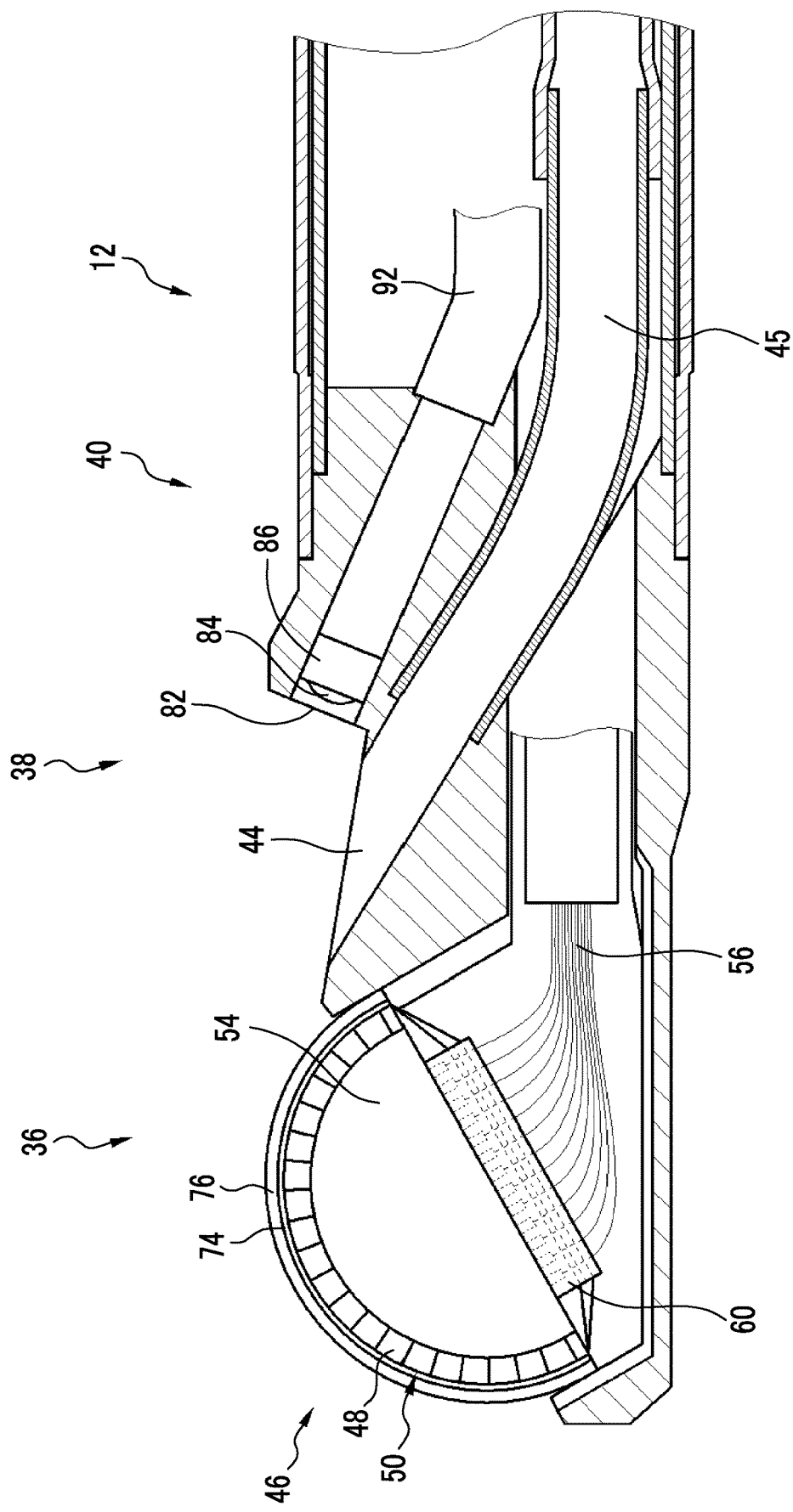
FIG. 3 is a diagram showing a cross section of the distal end portion of the insertion part of the ultrasound endoscope taken along the line I-I in FIG. 2.

The ultrasound endoscope 12 is an endoscope, and comprises an insertion part 22 to be inserted into the body cavity of a patient, an operation unit 24 operated by an operator (user), such as a doctor or a technician, and an ultrasound transducer unit 46 attached to a distal end portion 40 of the insertion part 22 (refer to FIGS. 2 and 3). By the function of the ultrasound endoscope 12, the operator can acquire an endoscope image of the inner wall of the body cavity of the patient and an ultrasound image of the observation target part.

Here, the "endoscope image" is an image obtained by imaging the inner wall of the body cavity of the patient using an optical method. The "ultrasound image" is an image obtained by receiving a reflected wave (echo) of an ultrasound wave transmitted from the inside of the body cavity of the patient to the observation target part and converting the reception signal into an image.

The ultrasound endoscope 12 will be described in detail later.

The ultrasound processor apparatus 14 is connected to the ultrasound endoscope 12 through a universal cord 26 and an ultrasound connector 32a provided at an end portion of the universal cord 26. The ultrasound processor apparatus 14 controls the ultrasound transducer unit 46 of the ultrasound endoscope 12 to transmit the ultrasound wave. In addition, the ultrasound processor apparatus 14 generates an ultrasound image by converting the reception signal in a case where the reflected wave (echo) of the transmitted ultrasound wave is received by the ultrasound transducer unit 46 into an image.

The ultrasound processor apparatus 14 will be described in detail later.

The endoscope processor apparatus 16 is connected to the ultrasound endoscope 12 through the universal cord 26 and an endoscope connector 32b provided at an end portion of the universal cord 26. The endoscope processor apparatus 16 generates an endoscope image by acquiring image data of an observation target adjacent part imaged by the ultrasound endoscope 12 (more specifically, a solid-state imaging element 86 to be described later) and performing predetermined image processing on the acquired image data.

Here, the "observation target adjacent part" is a portion of the inner wall of the body cavity of the patient that is adjacent to the observation target part.

In the present embodiment, the ultrasound processor apparatus 14 and the endoscope processor apparatus 16 are formed by two apparatuses (computers) provided separately. However, the invention is not limited thereto, and both the ultrasound processor apparatus 14 and the endoscope processor apparatus 16 may be formed by one apparatus.

The light source device 18 is connected to the ultrasound endoscope 12 through the universal cord 26 and a light source connector 32c provided at an end portion of the universal cord 26. The light source device 18 emits white light or specific wavelength light formed of three primary color light components of red light, green light, and blue light at the time of imaging the observation target adjacent part using the ultrasound endoscope 12. The light emitted from the light source device 18 propagates through the ultrasound endoscope 12 through a light guide (not shown) included in the universal cord 26, and is emitted from the ultrasound endoscope 12 (more specifically, an illumination window 88 to be described later). As a result, the observation target adjacent part is illuminated with the light from the light source device 18.

The monitor 20 is connected to the ultrasound processor apparatus 14, and the endoscope processor apparatus 16, and displays an ultrasound image generated by the ultrasound processor apparatus 14 and an endoscope image generated by the endoscope processor apparatus 16. As a display method of the ultrasound image and the endoscope image, either one of the images may be switched and displayed on the monitor 20, or both the images may be displayed at the same time. Display modes of the ultrasound image and the endoscope image will be described later.

In the present embodiment, the ultrasound image and the endoscope image are displayed on one monitor 20. However, a monitor for displaying the ultrasound image and a monitor for displaying the endoscope image may be separately provided. In addition, the ultrasound image and the endoscope image may be displayed in a display form other than the monitor 20. For example, the ultrasound image and the endoscope image may be displayed on a display of a terminal carried by the operator.

The console 100 is an apparatus provided for the operator to input information necessary for ultrasound diagnosis or for the operator to instruct the ultrasound processor apparatus 14 to start ultrasound diagnosis. The console 100 is configured to include, for example, a keyboard, a mouse, a trackball, a touch pad, and a touch panel. In a case where the console 100 is operated, a CPU (control circuit) 152 (refer to FIG. 4) of the ultrasound processor apparatus 14 controls each unit of the apparatus (for example, a reception circuit 142 and a transmission circuit 144 to be described later) according to the operation content.

Specifically, the operator inputs examination information (for example, examination order information including a date, an order number, and the like and patient information including a patient ID, a patient name, and the like) through the console 100 before starting the ultrasound diagnosis. In a case where the operator gives an instruction to start the ultrasound diagnosis through the console 100 after the input of the examination information is completed, the CPU 152 of the ultrasound processor apparatus 14 controls each unit of the ultrasound processor apparatus 14 so that the ultrasound diagnosis is performed based on the input examination information.

The operator can set various control parameters with the console 100 at the time of performing the ultrasound diagnosis. As the control parameters, for example, selection results of a live mode and a freeze mode, set values of the display depth (depth), selection results of an ultrasound image generation mode, and the like can be mentioned.

Here, the "live mode" is a mode in which ultrasound images (moving images) obtained at a predetermined frame rate are sequentially displayed (displayed in real time). The "freeze mode" is a mode in which an image (still image) of one frame of the ultrasound images (moving images) generated in the past is read out from a cine memory 150 to be described later and displayed.

There are a plurality of ultrasound image generation modes that can be selected in the present embodiment. Specifically, there are a brightness (B) mode, a color flow (CF) mode, and a pulse wave (PW) mode. The B mode is a mode in which a tomographic image is displayed by converting the amplitude of the ultrasound echo into a brightness. The CF mode is a mode in which average blood flow speed, flow fluctuation, strength of flow signal, flow power, and the like are mapped to various colors and displayed so as to be superimposed on a B mode image. The PW mode is a mode in which the speed (for example, blood flow speed) of the ultrasound echo source detected based on the transmission and reception of the pulse wave is displayed.

The ultrasound image generation modes described above are merely examples, and modes other than the above-described three kinds of modes, for example, an amplitude (A) mode and a motion (M) mode may be further included.

Next, the operation of the ultrasound diagnostic apparatus 10 will be described. The ultrasound diagnostic apparatus 10 performs an input step of inputting examination information, a diagnostic step of performing ultrasound diagnosis, and a standby step of waiting for preparation for ultrasound diagnosis and the like after the electric power is supplied. At the start of the ultrasound diagnostic apparatus 10, first, an input step is performed. In the input step, the operator operates the console 100 to input the examination information described above. After the end of the input of examination information, the diagnostic step is started in a case where the operator gives an instruction to start ultrasound diagnosis with the console 100. The standby step is performed until there is an instruction to start ultrasound diagnosis after the end of the input of examination information.

In the present embodiment, the operation mode of the ultrasound diagnostic apparatus 10 is set in performing each step after the input step. The operation mode includes a first mode and a second mode. The first mode is a normal mode in which ultrasound diagnosis is performed according to a normal procedure and polarization processing is not performed in a period (hereinafter, referred to as a non-diagnosis period) other than the execution period of ultrasound diagnosis. The second mode is a recovery mode in which ultrasound diagnosis is performed and polarization processing to be described below is performed in the non-diagnosis period. After the input step, the ultrasound diagnostic apparatus 10 operates according to one of the first mode and the second mode.

<<Configuration of Ultrasound Endoscope 12>>

Figure 4:
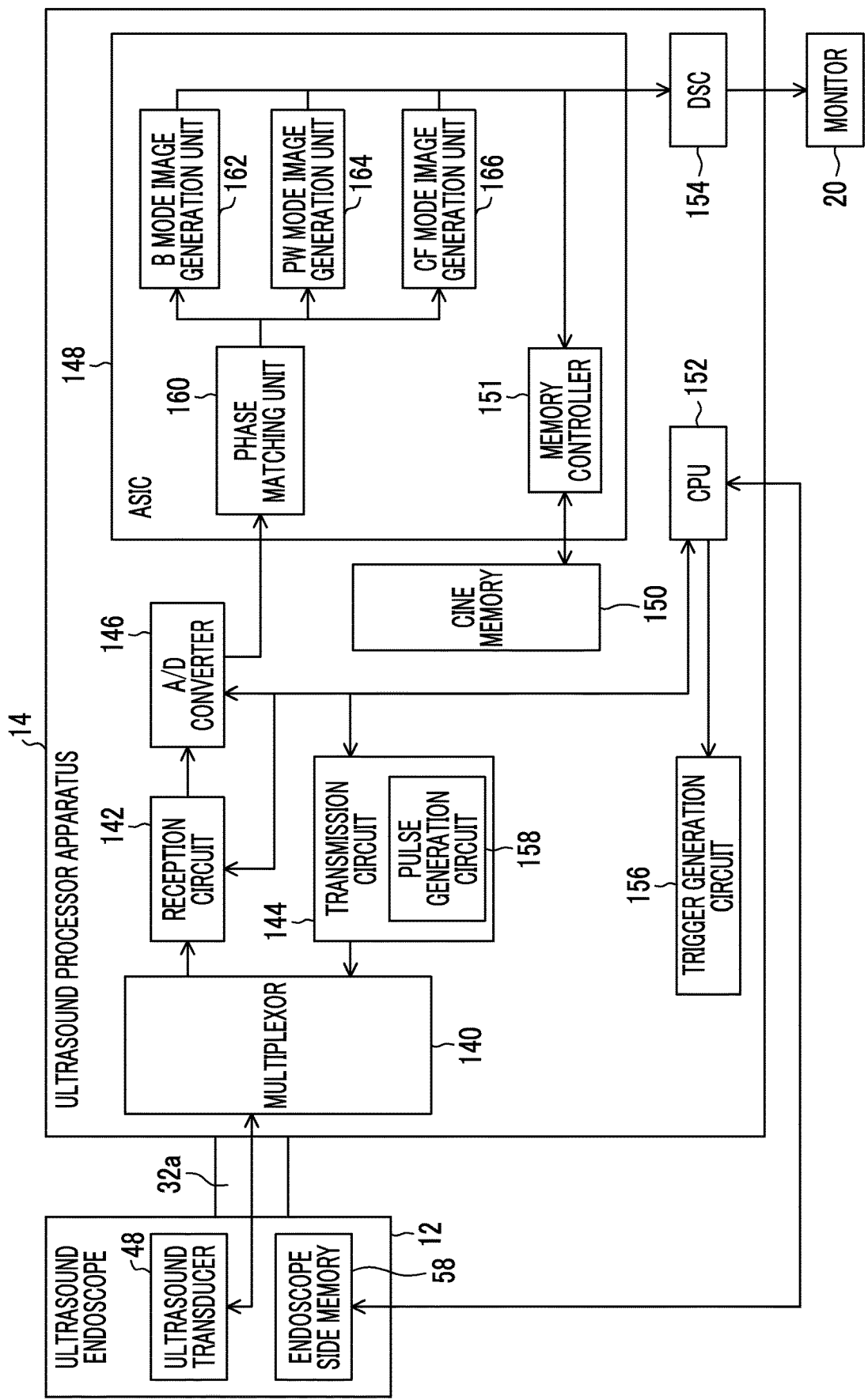
FIG. 4 is a block diagram showing the configuration of an ultrasound processor apparatus.

Next, the configuration of the ultrasound endoscope 12 will be described with reference to FIGS. 1 to 4. FIG. 2 is an enlarged plan view showing a distal end portion of an insertion part 22 of an ultrasound endoscope 12 and the periphery thereof. FIG. 3 is a cross-sectional view showing a cross section of the distal end portion 40 of the insertion part 22 of the ultrasound endoscope 12 taken along the line I-I in FIG. 2. FIG. 4 is a block diagram showing the configuration of an ultrasound processor apparatus 14.

As described above the ultrasound endoscope 12 has the insertion part 22 and the operation unit 24. As shown in FIG. 1, the insertion part 22 comprises the distal end portion 40, a bending portion 42, and a flexible portion 43 in order from the distal end side (free end side). As shown in FIG. 2, an ultrasound observation portion 36 and an endoscope observation portion 38 are provided in the distal end portion 40. As shown in FIG. 3, the ultrasound transducer unit 46 comprising a plurality of ultrasound transducers 48 is disposed in the ultrasound observation portion 36.

As shown in FIG. 2, a treatment tool lead-out port 44 is provided in the distal end portion 40. The treatment tool lead-out port 44 serves as an outlet of a treatment tool (not shown), such as forceps, an insertion needle, or a high frequency scalpel. In addition, the treatment tool lead-out port 44 serves as a suction port in the case of sucking aspirates, such as blood and body waste.

The bending portion 42 is a portion continuously provided on the more proximal side (side opposite to the side where the ultrasound transducer unit 46 is provided) than the distal end portion 40, and can bend freely. The flexible portion 43 is a portion connecting the bending portion 42 and the operation unit 24 to each other, has flexibility, and is provided so as to extend in an elongated state.

A plurality of pipe lines for air and water supply and a plurality of pipe lines for suction are formed in the insertion part 22 and the operation unit 24, respectively. In addition, a treatment tool channel 45 whose one end communicates with the treatment tool lead-out port 44 is formed in each of the insertion part 22 and the operation unit 24.

Next, the ultrasound observation portion 36, the endoscope observation portion 38, the water supply tank 21*a,* the suction pump 21*b,* and the operation unit 24 among the components of the ultrasound endoscope 12 will be described in detail.

(Ultrasound Observation Portion 36)

The ultrasound observation portion 36 is a portion provided to acquire an ultrasound image, and is disposed on the distal end side in the distal end portion 40 of the insertion part 22. As shown in FIG. 3, the ultrasound observation portion 36 comprises the ultrasound transducer unit 46, a plurality of coaxial cables 56, and a flexible printed circuit (FPC) 60.

The ultrasound transducer unit 46 corresponds to an ultrasound probe (probe), and transmits an ultrasound wave using an ultrasound transducer array 50, in which a plurality of ultrasound transducers 48 to be described later are arranged, in the body cavity of the patient, receives a reflected wave (echo) of the ultrasound wave reflected by the observation target part, and outputs a reception signal. The ultrasound transducer unit 46 according to the present embodiment is a convex type, and transmits an ultrasound wave radially (in an arc shape). However, the type (model) of the ultrasound transducer unit 46 is not particularly limited, and other types may be used as long as it is possible to transmit and receive ultrasound waves. For example, a sector type, a linear type, and a radial type may be used.

As shown in FIG. 3, the ultrasound transducer unit 46 is formed by laminating a backing material layer 54, an ultrasound transducer array 50, an acoustic matching layer 74, and an acoustic lens 76.

The ultrasound transducer array 50 includes a plurality of ultrasound transducers 48 (ultrasound transducers) arranged in a one-dimensional array. More specifically, the ultrasound transducer array 50 is formed by arranging N (for example, N=128) ultrasound transducers 48 at equal intervals in a convex bending shape along the axial direction of the distal end portion 40 (longitudinal axis direction of the insertion part 22). The ultrasound transducer array 50 may be one in which a plurality of ultrasound transducers 48 are disposed in a two-dimensional array.

Each of the N ultrasound transducers 48 is formed by disposing electrodes on both surfaces of a single crystal transducer that is a piezoelectric element. As the single crystal transducer, any of quartz, lithium niobate, lead magnesium niobate (PMN), lead zinc niobate (PZN), lead indium niobate (PIN), lead titanate (PT), lead magnesium niobate-lead titanate (PMN-PT), zinc niobate-lead titanate (PZN-PT), lithium tantalate, langasite, and zinc oxide can be used.

The electrodes is an individual electrode (not shown) individually provided for each of the plurality of ultrasound transducers 48 and a transducer ground (not shown) common to the plurality of ultrasound transducers 48. In addition, the electrodes are electrically connected to the ultrasound processor apparatus 14 through the coaxial cable 56 and the FPC 60.

The ultrasound transducer 48 according to the present embodiment needs to be driven (vibrated) at a relatively high frequency of 7 MHz to 8 MHz level in order to acquire an ultrasound image in the body cavity of the patient. For this reason, the thickness of the piezoelectric element forming the ultrasound transducer 48 is designed to be relatively small. For example, the thickness of the piezoelectric element forming the ultrasound transducer 48 is 75 μm to 125 μm, preferably 90 μm to 110 μm.

A diagnostic driving pulse that is a pulsed driving voltage is supplied from the ultrasound processor apparatus 14 to each ultrasound transducer 48, as an input signal (transmission signal), through the coaxial cable 56. In a case where the driving voltage is applied to the electrodes of the ultrasound transducer 48, the piezoelectric element expands and contracts to drive (vibrate) the ultrasound transducer 48. As a result, a pulsed ultrasound wave is output from the ultrasound transducer 48. In this case, the amplitude of the ultrasound wave output from the ultrasound transducer 48 has a magnitude corresponding to the intensity (output intensity) in a case where the ultrasound transducer 48 outputs the ultrasound wave. Here, the output intensity is defined as the magnitude of the sound pressure of the ultrasound wave output from the ultrasound transducer 48.

Each ultrasound transducer 48 vibrates (is driven) upon receiving the reflected wave (echo) of the ultrasound wave, and the piezoelectric element of each ultrasound transducer 48 generates an electric signal. The electric signal is output from each ultrasound transducer 48 to the ultrasound processor apparatus 14 as a reception signal of the ultrasound wave. In this case, the magnitude (voltage value) of the electric signal output from the ultrasound transducer 48 has a magnitude corresponding to the reception sensitivity in a case where the ultrasound transducer 48 receives the ultrasound wave. Here, the reception sensitivity is defined as a ratio of the amplitude of the electric signal, which is output from the ultrasound transducer 48 in response to reception of the ultrasound wave, to the amplitude of the ultrasound wave transmitted by the ultrasound transducer 48.

In the present embodiment, by sequentially driving the N ultrasound transducers 48 with an electronic switch such as a multiplexer 140 (refer to FIG. 4), an ultrasound scan occurs in a scanning range along the curved surface on which the ultrasound transducer array 50 is disposed, for example, in the range of about several tens of mm from the center of curvature of the curved surface. More specifically, in the case of acquiring a B mode image (tomographic image) as an ultrasound image, a driving voltage is supplied to m (for example, m=N/2) ultrasound transducers 48 (hereinafter, referred to as driving target transducers) arranged in series, among the N ultrasound transducers 48, by opening channel selection of the multiplexer 140. As a result, the m driving target transducers are driven, and an ultrasound wave is output from each driving target transducer of the opening channel. The ultrasound waves output from the m driving target transducers are immediately synthesized, and the composite wave (ultrasound beam) is transmitted to the observation target part. Thereafter, each of the m driving target transducers receives an ultrasound wave (echo) reflected at the observation target part, and outputs an electric signal (reception signal) corresponding to the reception sensitivity at that point in time.

Then, the above-described series of steps (that is, supply of a driving voltage, transmission and reception of ultrasound waves, and output of an electric signal) are repeatedly performed while shifting the position of the driving target transducer, among the N ultrasound transducers 48, one by one (one ultrasound transducer 48 at a time). Specifically, the above-described series of steps are started from m driving target transducers on both sides of the ultrasound transducer 48 located at one end among the N ultrasound transducers 48. Then, the above-described series of steps are repeated each time the position of the driving target transducer is shifted due to switching of the opening channel by the multiplexer 140. Finally, the above-described series of steps are repeatedly performed a total of N times up to m driving target transducers on both sides of the ultrasound transducer 48 located at the other end among the N ultrasound transducers 48.

The backing material layer 54 supports each ultrasound transducer 48 of the ultrasound transducer array 50 from the back surface side. In addition, the backing material layer 54 has a function of attenuating ultrasound waves propagating to the backing material layer 54 side among ultrasound waves emitted from the ultrasound transducer 48 or ultrasound waves (echoes) reflected by the observation target part. The backing material is a material having rigidity, such as hard rubber, and an ultrasound damping material (ferrite, ceramics, and the like) is added as necessary.

The acoustic matching layer 74 is superimposed on the ultrasound transducer array 50, and is provided for acoustic impedance matching between the body of the patient and the ultrasound transducer 48. Since the acoustic matching layer 74 is provided, it is possible to increase the transmittance of the ultrasound wave. As a material of the acoustic matching layer 74, it is possible to use various organic materials whose acoustic impedance values are closer to that of the body of the patient than the piezoelectric element of the ultrasound transducer 48. Specific examples of the material of the acoustic matching layer 74 include epoxy resin, silicone rubber, polyimide, polyethylene, and the like.

The acoustic lens 76 superimposed on the acoustic matching layer 74 converges ultrasound waves emitted from the ultrasound transducer array 50 toward the observation target part. The acoustic lens 76 is formed of, for example, silicon resin (millable silicone rubber (HTV rubber), liquid silicone rubber (RTV rubber), and the like), butadiene resin, and polyurethane resin, and powders of titanium oxide, alumina, silica, and the like are mixed as necessary.

The FPC 60 is electrically connected to the electrode of each ultrasound transducer 48. Each of the plurality of coaxial cables 56 is wired to the FPC 60 at one end thereof. Then, in a case where the ultrasound endoscope 12 is connected to the ultrasound processor apparatus 14 through the ultrasound connector 32a, each of the plurality of coaxial cables 56 is electrically connected to the ultrasound processor apparatus 14 at the other end (side opposite to the FPC 60).

In the present embodiment, the ultrasound endoscope 12 comprises an endoscope side memory 58 (refer to FIG. 4). The endoscope side memory 58 stores driving times of the plurality of ultrasound transducers 48 at the time of ultrasound diagnosis. Strictly speaking, in the endoscope side memory 58, the cumulative driving time of the driving target transducer after the operation mode of the ultrasound diagnostic apparatus 10 becomes the first mode, among the plurality of ultrasound transducers 48, is stored.

In the present embodiment, an execution period of ultrasound diagnosis, that is, a period from the start of acquisition of an ultrasound image (moving image) to the end thereof (more specifically, a time during which ultrasound diagnosis is performed in the live mode), is set as the cumulative driving time. However, the invention is not limited thereto, and the time for which the driving voltage is supplied to the driving target transducer may be set as the cumulative driving time.

In a state in which the ultrasound endoscope 12 is connected to the ultrasound processor apparatus 14, the CPU 152 of the ultrasound processor apparatus 14 can access the endoscope side memory 58 to read the cumulative driving time stored in the endoscope side memory 58. In addition, the CPU 152 of the ultrasound processor apparatus 14 rewrites the cumulative driving time stored in the endoscope side memory 58 to a default value, or updates the stored cumulative driving time to a new cumulative driving time in a case where the cumulative driving time changes with the execution of ultrasound diagnosis.

(Endoscope Observation Portion 38)

The endoscope observation portion 38 is a portion provided to acquire an endoscope image, and is disposed on the more proximal side than ultrasound observation portion 36 in the distal end portion 40 of the insertion part 22. As shown in FIGS. 2 and 3, the endoscope observation portion 38 includes the observation window 82, an objective lens 84, the solid-state imaging element 86, the illumination window 88, the cleaning nozzle 90, a wiring cable 92, and the like.

The observation window 82 is attached so as to be inclined with respect to the axial direction (longitudinal axis direction of the insertion part 22) at the distal end portion 40 of the insertion part 22. Light incident through the observation window 82 and reflected at the observation target adjacent part is focused on the imaging surface of the solid-state imaging element 86 by the objective lens 84.

The solid-state imaging element 86 photoelectrically converts the reflected light of the observation target adjacent part, which is focused on the imaging surface after being transmitted through the observation window 82 and the objective lens 84, and outputs an imaging signal. As the solid-state imaging element 86, it is possible to use a charge coupled device (CCD), a complementary metal oxide semiconductor (CMOS), and the like. The captured image signal output from the solid-state imaging element 86 is transmitted to the endoscope processor apparatus 16 by the universal cord 26 through the wiring cable 92 extending from the insertion part 22 to the operation unit 24.

The illumination window 88 is provided at both side positions of the observation window 82. An exit end of a light guide (not shown) is connected to the illumination window 88. The light guide extends from the insertion part 22 to the operation unit 24, and its incidence end is connected to the light source device 18 connected through the universal cord 26. The illumination light emitted from the light source device 18 is transmitted through the light guide and is emitted from the illumination window 88 toward the observation target adjacent part.

The cleaning nozzle 90 is an ejection hole formed at the distal end portion 40 of the insertion part 22 in order to clean the surfaces of the observation window 82 and the illumination window 88. From the cleaning nozzle 90, air or cleaning liquid is ejected toward the observation window 82 and the illumination window 88. In the present embodiment, the cleaning liquid ejected from the cleaning nozzle 90 is water, in particular, degassed water. However, the cleaning liquid is not particularly limited, and other liquids, for example, normal water (water that is not degassed) may be used.

(Water Supply Tank 21a and Suction Pump 21b)

The water supply tank 21a is a tank that stores degassed water, and is connected to the light source connector 32c by an air and water supply tube 34a. Degassed water is used as a cleaning liquid ejected from the cleaning nozzle 90.

The suction pump 21b sucks aspirates (including degassed water supplied for cleaning) inside the body cavity through the treatment tool lead-out port 44. The suction pump 21b is connected to the light source connector 32c by a suction tube 34b. The ultrasound diagnostic apparatus 10 may comprise an air supply pump for supplying air to a predetermined air supply destination and the like.

In the insertion part 22 and the operation unit 24, the treatment tool channel 45 and an air and water supply pipe line (not shown) 62 are provided.

The treatment tool channel 45 communicates between a treatment tool insertion port 30 and the treatment tool lead-out port 44 provided in the operation unit 24. The treatment tool channel 45 is connected to a suction button 28b provided in the operation unit 24. The suction button 28b is connected to the suction pump 21b in addition to the treatment tool channel 45.

The air and water supply pipe line 62 communicates with the cleaning nozzle 90 at one end side, and is connected to an air and water supply button 28a provided in the operation unit 24 at the other end side. The air and water supply button 28a is connected to the water supply tank 21a in addition to the air and water supply pipe line.

(Operation Unit 24)

The operation unit 24 is a unit operated by the operator at the start of ultrasound diagnosis, during diagnosis, at the end of diagnostic, and one end of the universal cord 26 is connected to one end of the operation unit 24. As shown in FIG. 1, the operation unit 24 has the air and water supply button 28a, the suction button 28b, a pair of angle knobs 29, and a treatment tool insertion port (forceps port) 30.

In a case where each of the pair of angle knobs 29 is rotated, the bending portion 42 is remotely operated to be bent and deformed. By this deformation operation, the distal end portion 40 of the insertion part 22 in which the ultrasound observation portion 36 and the endoscope observation portion 38 are provided can be directed in a desired direction.

The treatment tool insertion port 30 is a hole formed to insert a treatment tool (not shown), such as forceps, and communicates with the treatment tool lead-out port 44 through the treatment tool channel 45. The treatment tool inserted into the treatment tool insertion port 30 is introduced into the body cavity from the treatment tool lead-out port 44 after passing through the treatment tool channel 45.

The air and water supply button 28a and the suction button 28b are two-stage switching type push buttons, and are operated to switch the opening and closing of the pipe line provided inside each of the insertion part 22 and the operation unit 24.

<<Configuration of Ultrasound Processor Apparatus 14>>

The ultrasound processor apparatus 14 causes the ultrasound transducer unit 46 to transmit and receive ultrasound waves, and generates an ultrasound image by converting the reception signal, which is output from the ultrasound transducer 48 (specifically, a driving target element) at the time of ultrasound wave reception, into an image. In addition, the ultrasound processor apparatus 14 displays the generated ultrasound image on the monitor 20.

In the present embodiment, the ultrasound processor apparatus 14 supplies a polarization voltage to a polarization target transducer, among the N ultrasound transducers 48, to polarize the polarization target transducer. By performing the polarization processing, the depolarized ultrasound transducer 48 can be polarized again by repeating the ultrasound diagnosis. As a result, it is possible to restore the reception sensitivity of the ultrasound transducer 48 with respect to ultrasound waves to a satisfactory level.

As shown in FIG. 4, the ultrasound processor apparatus 14 has the multiplexer 140, the reception circuit 142, the transmission circuit 144, an A/D converter 146, an application specific integrated circuit (ASIC) 148, the cine memory 150, a notification circuit 156, a central processing unit (CPU) 152, and a digital scan converter (DSC) 154.

The reception circuit 142 and the transmission circuit 144 are electrically connected to the ultrasound transducer array 50 of the ultrasound endoscope 12. The multiplexer 140 selects a maximum of m driving target transducers from the N ultrasound transducers 48, and opens their channels.

The transmission circuit 144 is configured to include a field programmable gate array (FPGA), a pulser (pulse generation circuit 158), a switch (SW), and the like, and is connected to the multiplexer 140 (MUX). Instead of the FPGA, an application specific integrated circuit (ASIC) may be used.

The transmission circuit 144 is a circuit that supplies a driving voltage for ultrasound wave transmission to the driving target transducers selected by the multiplexer 140, according to the control signal transmitted from the CPU 152, in order to transmit ultrasound waves from the ultrasound transducer unit 46. The driving voltage is a pulsed voltage signal (transmission signal), and is applied to the electrodes of the driving target transducers through the universal cord 26 and the coaxial cable 56.

The transmission circuit 144 has a pulse generation circuit 158 that generates a transmission signal based on a control signal. Under the control of the CPU 152, a transmission signal for driving a plurality of ultrasound transducers 48 to generate ultrasound waves is generated using the pulse generation circuit 158, and the generated transmission signal is supplied to the plurality of ultrasound transducers 48.

In addition, under the control of the CPU 152, in the case of performing ultrasound diagnosis, the transmission circuit 144 generates a first transmission signal (diagnostic driving pulse) having a driving voltage for performing ultrasound diagnosis using the pulse generation circuit 158. In addition, under the control of the CPU 152, in the case of performing polarization processing, a second transmission signal (polarization driving pulse) having a polarization voltage for performing polarization processing is generated using the same pulse generation circuit 158 as in the case of generating the first transmission signal. The first and second transmission signals are pulse waves.

In the invention, the polarization driving pulse is generated by the pulse generation circuit 158 of the transmission circuit 144 that generates a diagnostic driving pulse for acquiring an ultrasound image. That is, the transmission circuit 144 has the same circuit configuration as an existing transmission circuit that does not have a new circuit configuration for generating the polarization driving pulse. Therefore, the polarization driving pulse (second transmission signal) applied to the ultrasound transducer 48 at the time of polarization processing is generated using the diagnostic driving pulse (first transmission signal) applied to the ultrasound transducer 48 at the time of acquisition of an ultrasound image.

Here, although the voltage ranges of the first transmission signal and the second transmission signal generated by the same pulse generation circuit 158 are the same, the output voltage (driving voltage) of the first transmission signal and the output voltage (polarization voltage) of the second transmission signal can be different voltage values within the adjustable range of the output voltage. For example, the output voltages of the first transmission signal and the second transmission signal can be the same voltage, or the output voltage of the second transmission signal can be larger than the output voltage of the first transmission signal.

Although the details will be described later, the polarization driving pulse (main lobe) is a driving pulse in a frequency band different from the probe frequency band of the diagnostic driving pulse. More specifically, reception signals of the plurality of ultrasound transducers 48 within the frequency band of the first ultrasound wave generated by the first transmission signal (diagnostic driving pulse) and reception signals of the plurality of ultrasound transducers 48 within the frequency band of the main lobe of the second ultrasound wave generated by the second transmission signal (polarization driving pulse) have different band characteristics. For example, as shown in FIG. 11B, it is preferable that the band characteristics of the reception signals of the plurality of ultrasound transducers 48 within the frequency band of the first ultrasound wave generated by the first transmission signal and the band characteristics of the reception signals of the plurality of ultrasound transducers 48 within the frequency band of the main lobe of the second ultrasound wave generated by the second transmission signal do not overlap at a level of −20 dB or more.

From the above, the invention has an existing transmission circuit configuration. Using the transmission circuit 144 for the same driving pulse output as acquisition of an ultrasound image, a polarization driving pulse in a frequency band different from the probe frequency band of the diagnostic driving pulse is output, and polarization processing of the ultrasound transducer 48 of the ultrasound endoscope 12 is performed at a time different from the time for acquiring an ultrasound image.

The magnitude (voltage value or potential) and the supply time of the polarization voltage of the polarization driving pulse are set to appropriate values, which satisfy the conditions for obtaining the repolarization effect, by the CPU 152 in accordance with the specification of the ultrasound transducer 48 (specifically, the thickness and the material of the ultrasound transducer 48) provided in the ultrasound endoscope 12 connected to the ultrasound processor apparatus 14. Thereafter, the CPU 152 performs polarization processing based on the set values described above.

That is, in the invention, in the case of acquiring an ultrasound image, the CPU (control circuit) 152 controls the transmission circuit 144 (pulse generation circuit 158) to generate a diagnostic driving pulse (first transmission signal) to be applied to each of the plurality of ultrasound transducers 48 that generate ultrasound waves for acquisition of an ultrasound image.

On the other hand, in the case of performing polarization processing, in order to perform polarization processing of the plurality of ultrasound transducers 48, the CPU (control circuit) 152 controls the transmission circuit 144 (pulse generation circuit 158) to generate a polarization driving pulse (second transmission signal) having a frequency different from the probe frequency band as an ultrasound probe (ultrasound transducer unit 46) for acquiring an ultrasound image.

As a result, in the invention, in the case of performing polarization processing, the polarization driving pulse is applied to the plurality of ultrasound transducers 48, and the polarization processing of the plurality of ultrasound transducers 48 is performed by the polarization driving pulse.

Then, the reception circuit 142 is a circuit that receives an electric signal output from the driving target transducer that has received an ultrasound wave (echo), that is, a reception signal. In addition, according to the control signal transmitted from the CPU 152, the reception circuit 142 amplifies the reception signal received from the ultrasound transducer 48 and transmits the amplified signal to the A/D converter 146. The A/D converter 146 is connected to the reception circuit 142, and converts the reception signal received from the reception circuit 142 from an analog signal to a digital signal and outputs the converted digital signal to the ASIC 148.

The ASIC 148 is connected to the A/D converter 146. As shown in FIG. 4, the ASIC 148 forms a phase matching unit 160, a B mode image generation unit 162, a PW mode image generation unit 164, a CF mode image generation unit 166, and a memory controller 151.

In the present embodiment, the above-described functions (specifically, the phase matching unit 160, the B mode image generation unit 162, the PW mode image generation unit 164, the CF mode image generation unit 166, and the memory controller 151) are realized by a hardware circuit, such as the ASIC 148. However, the invention is not limited thereto. The above-described functions may be realized by making the central processing unit (CPU) and software (computer program) for executing various kinds of data processing cooperate with each other.

The phase matching unit 160 performs processing for phasing addition (addition after matching the phases of reception data) by giving a delay time to the reception signal (reception data) digitized by the A/D converter 146. By the phasing addition processing, a sound ray signal with narrowed focus of the ultrasound echo is generated.

The B mode image generation unit 162, the PW mode image generation unit 164, and the CF mode image generation unit 166 generate an ultrasound image based on the electric signal (strictly speaking, the sound ray signal generated by phasing and adding the reception data) that is output from the driving target transducer among the plurality of ultrasound transducers 48 in a case where the ultrasound transducer unit 46 receives the ultrasound wave.

The B mode image generation unit 162 is an image generation unit that generates a B mode image that is a tomographic image of the inside of the patient (inside of the body cavity). For the sequentially generated sound ray signals, the B mode image generation unit 162 corrects the attenuation due to the propagation distance according to the depth of the reflection position of the ultrasound wave by sensitivity time control (STC). The B mode image generation unit 162 performs envelope detection processing and logarithm (Log) compression processing on the corrected sound ray signal, thereby generating a B mode image (image signal).

The PW mode image generation unit 164 is an image generation unit that generates an image showing the speed of blood flow in a predetermined direction. The PW mode image generation unit 164 extracts a frequency component by applying a fast Fourier transform to a plurality of sound ray signals in the same direction among the sound ray signals sequentially generated by the phase matching unit 160. Thereafter, the PW mode image generation unit 164 calculates the speed of blood flow from the extracted frequency component, and generates a PW mode image (image signal) showing the calculated speed of blood flow.

The CF mode image generation unit 166 is an image generation unit that generates an image showing blood flow information in a predetermined direction. The CF mode image generation unit 166 generates an image signal indicating the blood flow information by calculating the auto-correlation between a plurality of sound ray signals in the same direction among the sound ray signals sequentially generated by the phase matching unit 160. Thereafter, based on the image signal described above, the CF mode image generation unit 166 generates a CF mode image (image signal) as a color image in which the blood flow information is superimposed on the B mode image signal generated by the B mode image generation unit 162.

The memory controller 151 stores the image signal generated by the B mode image generation unit 162, the PW mode image generation unit 164, or the CF mode image generation unit 166 in the cine memory 150.

The DSC 154 is connected to the ASIC 148, and converts (raster conversion) the signal of the image generated by the B mode image generation unit 162, the PW mode image generation unit 164, or the CF mode image generation unit 166 into an image signal according to a normal television signal scanning method, performs various kinds of required image processing, such as gradation processing, on the image signal, and then outputs an obtained signal to the monitor 20.

The cine memory 150 has a capacity for storing an image signal for one frame or several frames. The image signal generated by the ASIC 148 is output to the DSC 154, and is also stored in the cine memory 150 by the memory controller 151. In the freeze mode, the memory controller 151 reads the image signal stored in the cine memory 150 and outputs the read image signal to the DSC 154. As a result, an ultrasound image (still image) based on the image signal read from the cine memory 150 is displayed on the monitor 20.

The notification circuit 156 is connected to the CPU 152. In the second mode, under the control of the CPU 152, the notification circuit 156 notifies the user that polarization processing is being performed in the case of the third display mode to be described later. The notification method is not particularly limited. For example, a message indicating that polarization processing is being performed may be displayed on the monitor 20, or notification may be provided using a sound, or it may be notified that polarization processing is being performed using a display lamp or the like.

The CPU 152 functions as a controller that controls each unit of the ultrasound processor apparatus 14. The CPU 152 is connected to the reception circuit 142, the transmission circuit 144, the A/D converter 146, and the ASIC 148 to control these devices. Specifically, the CPU 152 is connected to the console 100, and controls each unit of the ultrasound processor apparatus 14 according to examination information, control parameters, and the like input through the console 100.

The CPU 152 automatically recognizes the ultrasound endoscope 12 based on a method, such as Plug and Play (PnP), in a case where the ultrasound endoscope 12 is connected to the ultrasound processor apparatus 14 through the ultrasound connector 32a.

Thereafter, the CPU 152 accesses the endoscope side memory 58 of the ultrasound endoscope 12 to read the cumulative driving time stored in the endoscope side memory 58. In addition, the CPU 152 accesses the endoscope side memory 58 at the end of the ultrasound diagnosis, and updates the cumulative driving time stored in the endoscope side memory 58 to a value obtained by adding the time required for the ultrasound diagnosis performed immediately before to the cumulative driving time stored in the endoscope side memory 58.

In the present embodiment, the cumulative driving time is stored on the ultrasound endoscope 12 side. However, the invention is not limited thereto, and the cumulative driving time may be stored on the ultrasound processor apparatus 14 side for each ultrasound endoscope 12.

In addition, while the operation mode of the ultrasound diagnostic apparatus 10 is the second mode, the CPU 152 controls the transmission circuit 144 to perform polarization processing using the non-diagnosis period. More specifically, in a case where the cumulative driving time of the plurality of ultrasound transducers 48 for performing ultrasound diagnosis, in which a driving voltage is supplied to the driving target transducer, becomes equal to or longer than a specified time, the CPU 152 controls the transmission circuit 144 (pulse generation circuit 158) to perform polarization processing on the plurality of ultrasound transducers 48 in a period other than the execution period of ultrasound diagnosis, that is, in a non-diagnosis period during which transmission of ultrasound waves and reception of reflected waves for performing ultrasound diagnosis are not performed.

The specified time is a time set in advance, and is recorded on the ultrasound processor apparatus 14 side. The specified time is any time, and may be on the order of several hours or on the order of several frame times. The specified time may be different for each ultrasound endoscope 12, or may be a value common to the ultrasound endoscopes 12. A time of a default value may be set as the specified time, or the operator may set any specified time through the console 100.

<<Operation Example of Ultrasound Diagnostic Apparatus 10>>

Figure 5:
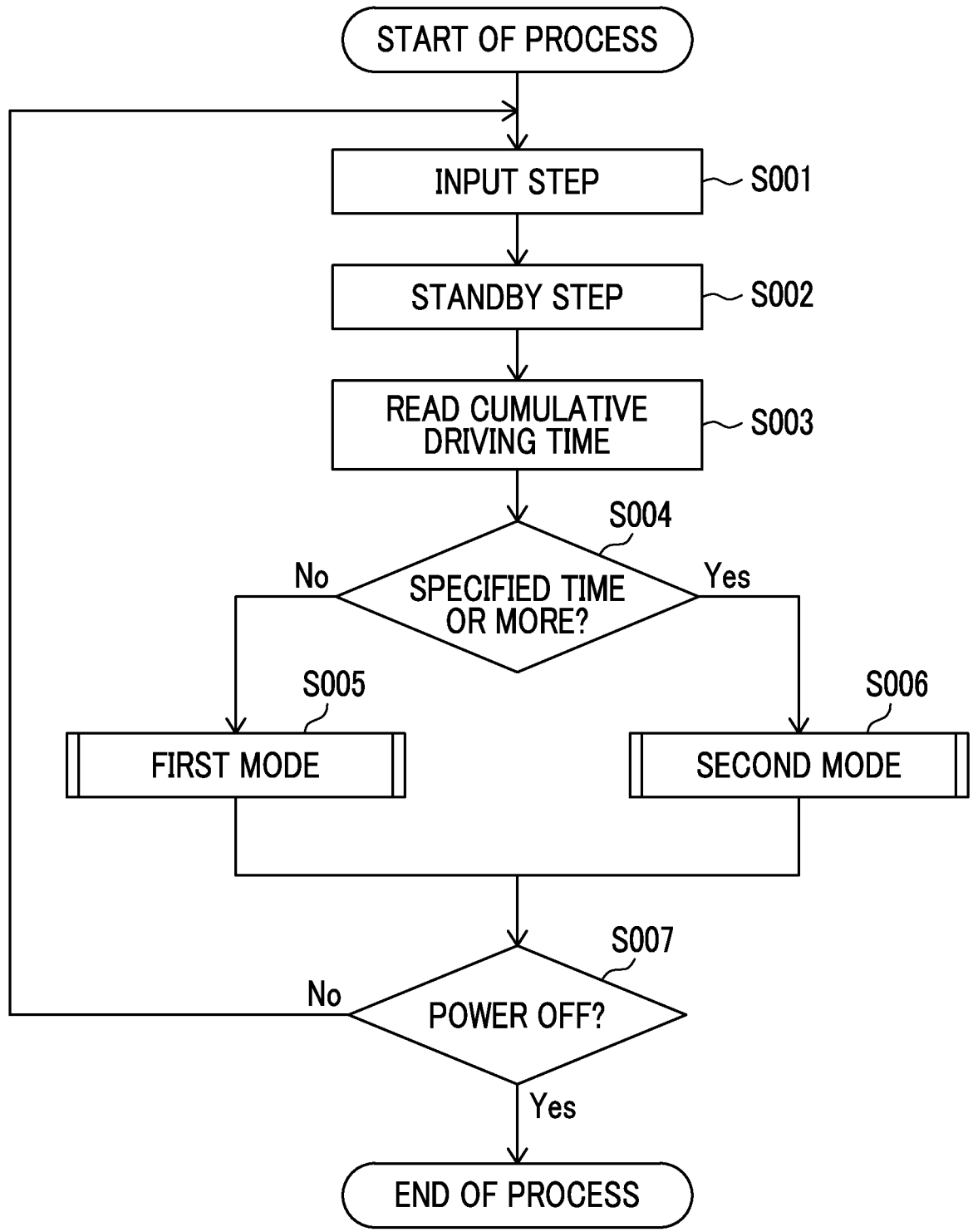
FIG. 5 is a diagram showing the flow of a diagnostic process using the ultrasound diagnostic apparatus.
Figure 6:
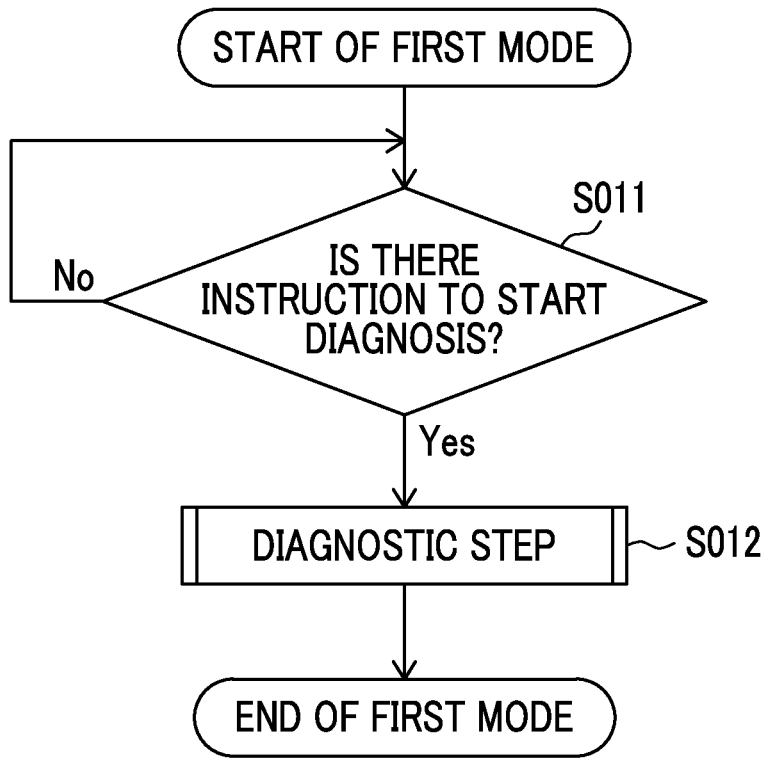
FIG. 6 is a diagram showing the flow of a diagnostic process in a first mode.
Figure 7:
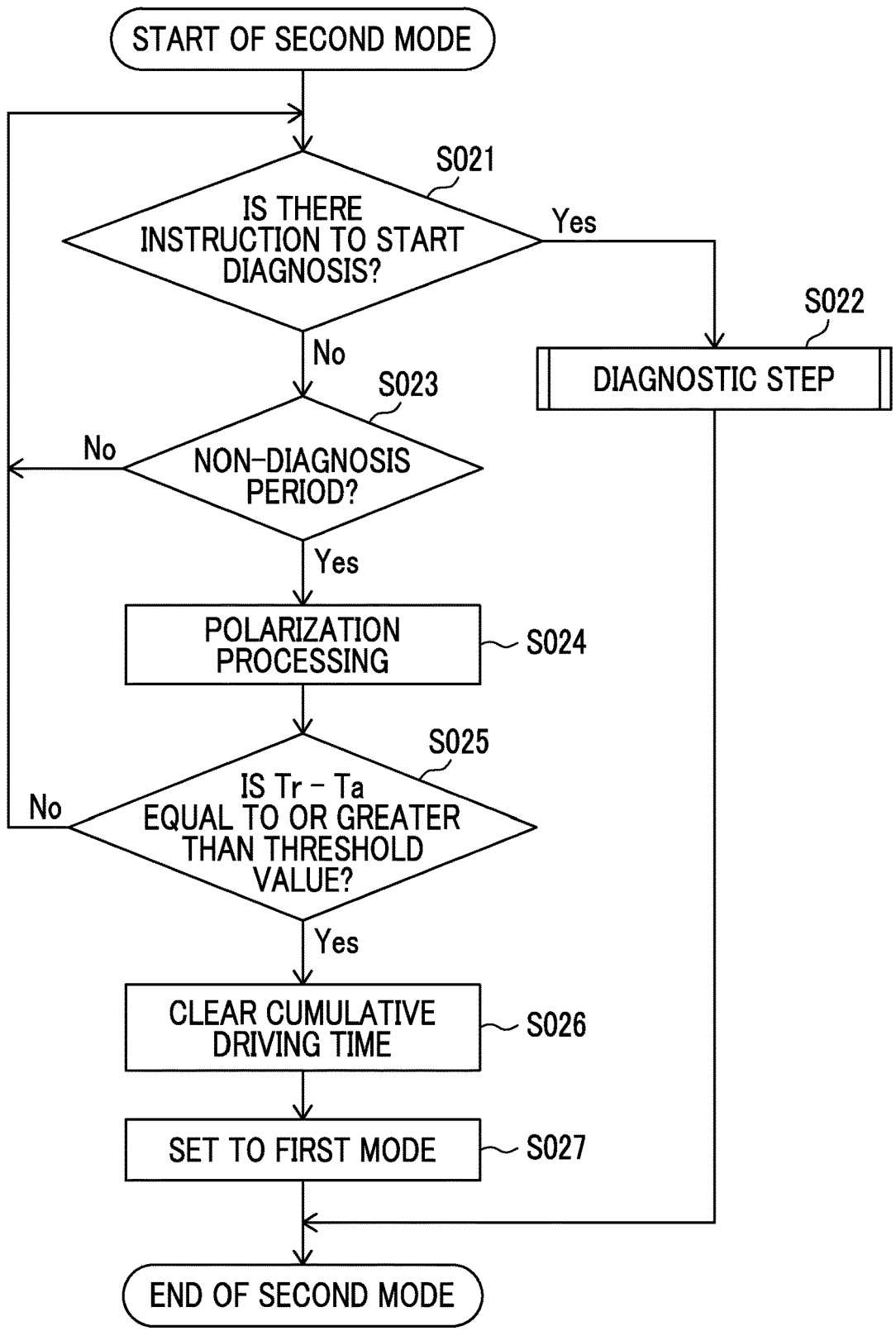
FIG. 7 is a diagram showing the flow of a diagnostic process in a second mode.
Figure 8:
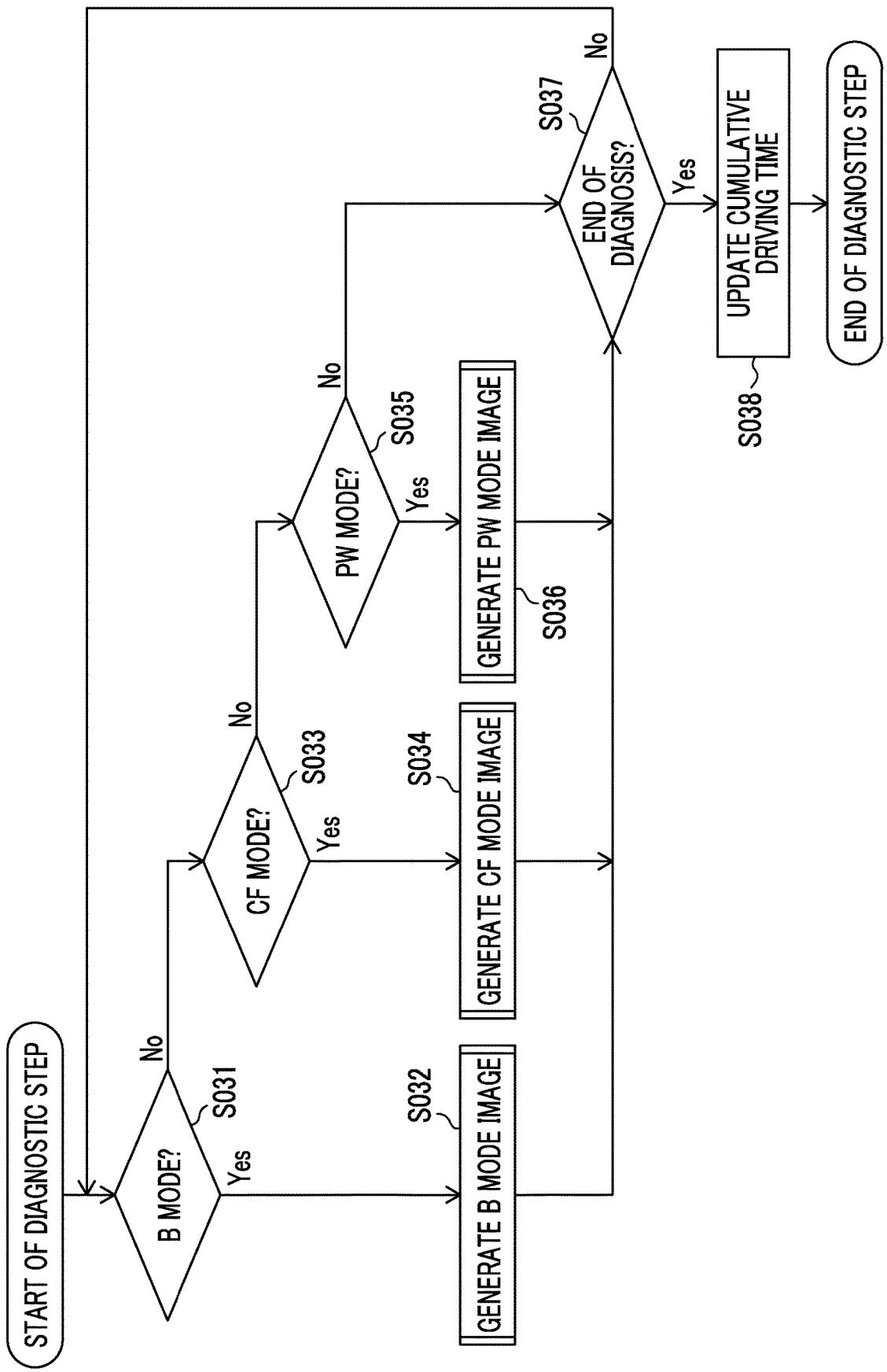
FIG. 8 is a diagram showing the procedure of a diagnostic step in the diagnostic process.

Next, as an operation example of the ultrasound diagnostic apparatus 10, a flow of a series of processes relevant to ultrasound diagnosis (hereinafter, also referred to as diagnostic process) will be described with reference to FIGS. 5 to 8. FIG. 5 is a diagram showing the flow of the diagnostic process using the ultrasound diagnostic apparatus 10. FIG. 6 is a diagram showing the flow of the diagnostic process in the first mode, and FIG. 7 is a diagram showing the flow of diagnostic process in the second mode. FIG. 8 is a diagram showing the procedure of a diagnostic step in the diagnostic process.

In a case where each unit of the ultrasound diagnostic apparatus 10 is powered on in a state in which the ultrasound endoscope 12 is connected to the ultrasound processor apparatus 14, the endoscope processor apparatus 16, and the light source device 18, the diagnostic process starts with the power-ON as a trigger. In the diagnostic process, as shown in FIG. 5, an input step is performed first (S001). In the input step, the operator inputs examination information, control parameters, and the like through the console 100. In a case where the input step is completed, a standby step is performed until there is an instruction to start diagnosis (S002). Using the standby step, the CPU 152 of the ultrasound processor apparatus 14 reads a cumulative driving time from the endoscope side memory 58 of the ultrasound endoscope 12 (S003).

Thereafter, the CPU 152 determines whether or not the read cumulative driving time is equal to or longer than the specified time (S004).

In a case where it is determined that the cumulative driving time is less than the specified time (No in S004), the CPU 152 sets the operation mode of the ultrasound diagnostic apparatus 10 to the first mode (S005). In the present embodiment, it is assumed that the operation mode at the initial setting stage is set to the first mode.

In a case where the operation mode is set to the first mode, normal steps in the case of performing ultrasound diagnosis are performed according to steps shown in FIG. 6. Specifically, first, it is determined whether or not there is a diagnosis start instruction from the operator (S011). In a case where there is no diagnosis start instruction from the operator (No in S011), the process returns to step S011 to repeat the operation described above. In a case where there is a diagnosis start instruction from the operator (Yes in S011), the CPU 152 controls each unit of the ultrasound processor apparatus 14 to perform a diagnostic step (S012).

The diagnostic step is performed according to steps shown in FIG. 8. That is, in a case where the designated image generation mode is the B mode (Yes in S031), each unit of the ultrasound processor apparatus 14 is controlled so as to generate a B mode image (S032). In a case where the designated image generation mode is not the B mode (No in S031) but the CF mode (Yes in S033), each unit of the ultrasound processor apparatus 14 is controlled so as to generate a CF mode image (S034). In a case where the designated image generation mode is not the CF mode (No in S033) but the PW mode (Yes in S035), each unit of the ultrasound processor apparatus 14 is controlled so as to generate a PW mode image (S036). In a case where the designated image generation mode is not the PW mode (No in S035), the process proceeds to step S037.

Then, the CPU 152 determines whether or not the ultrasound diagnosis has ended (S037). In a case where the ultrasound diagnosis has not ended (No in S037), the process returns to step S031, and the generation of an ultrasound image in each image generation mode is repeatedly performed until the diagnosis end conditions are satisfied. As the diagnosis end conditions, for example, the operator gives an instruction to end the diagnosis through the console 100.

On the other hand, in a case where the diagnosis end conditions are satisfied (Yes in S037), the CPU 152 adds the time required for the ultrasound diagnosis performed so far to the cumulative driving time read out from the endoscope side memory 58 in step S003, and updates the cumulative driving time stored in the endoscope side memory 58 to the cumulative driving time after the addition (S038). The diagnostic step ends at a point in time at which the series of steps (steps S031 to S038) in the diagnostic step end.

Then, returning to FIG. 5, it is determined whether or not each unit of the ultrasound diagnostic apparatus 10 is powered off (S007). In a case where each unit of the ultrasound diagnostic apparatus 10 is powered off (Yes in S007), the diagnostic process ends. On the other hand, in a case where the power of each unit of the ultrasound diagnostic apparatus 10 is maintained in the ON state (No in S007), the process returns to step S001, and each step of the diagnostic process described above is repeated.

On the other hand, in a case where it is determined that the cumulative driving time read from the endoscope side memory 58 is equal to or longer than the specified time in step S004, that is, in a case where the cumulative driving time of the plurality of ultrasound transducers for performing ultrasound diagnosis becomes equal to or longer than the specified time in the first mode (Yes in S004), the CPU 152 shifts the operation mode of the ultrasound diagnostic apparatus 10 from the first mode to the second mode (S006). While the operation mode is the second mode, ultrasound diagnosis is performed, and polarization processing is performed during the non-diagnosis period as described above. That is, in the present embodiment, the polarization voltage is supplied to the polarization target transducer only in a case where the operation mode is the second mode.

Figure 9:
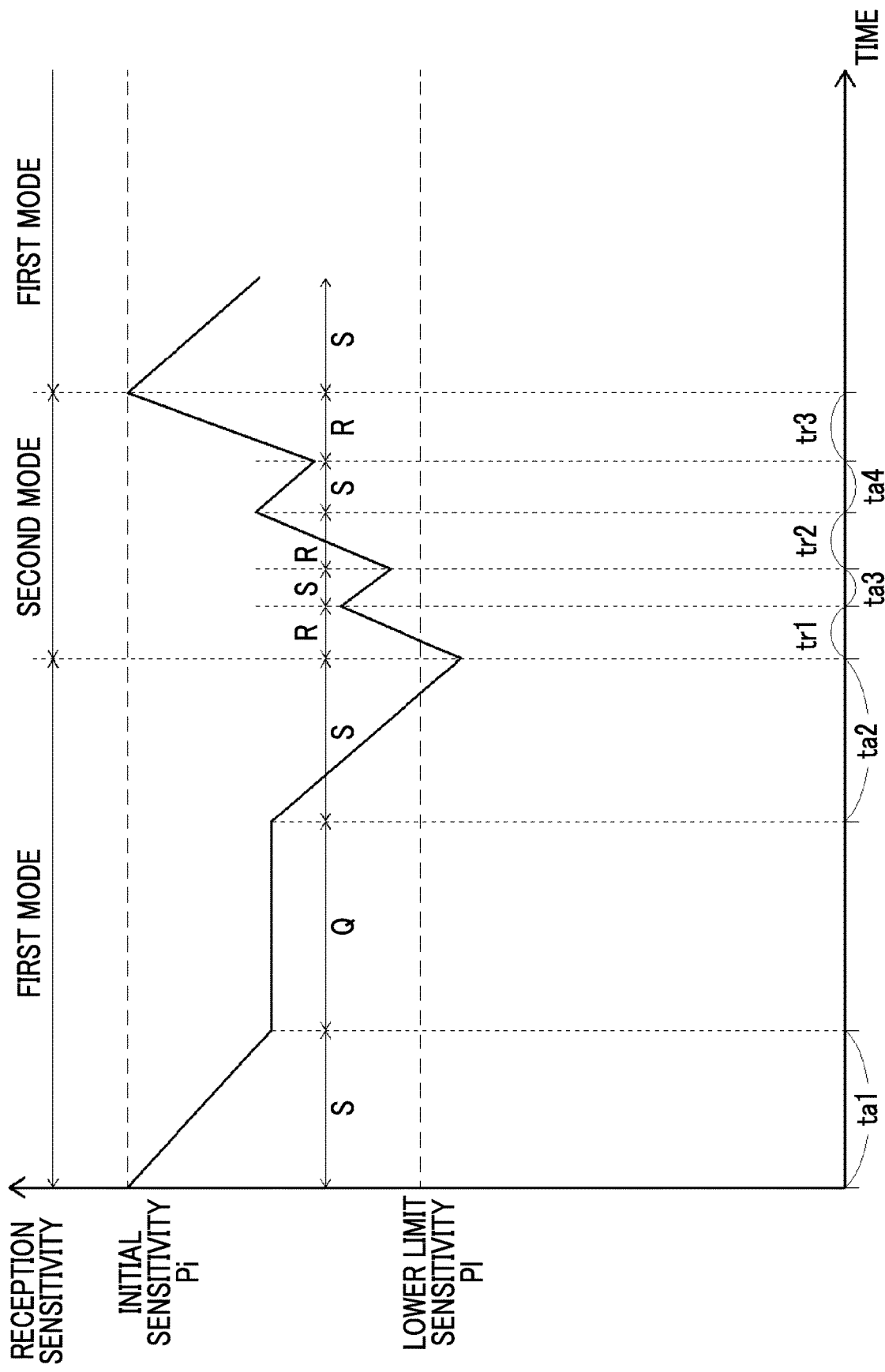
FIG. 9 is an explanatory diagram showing the relationship between the cumulative driving time and the polarization processing execution time of an ultrasound transducer and the reception sensitivity of the ultrasound transducer.

The reason why such a configuration is adopted will be described below with reference to FIG. 9. FIG. 9 is an explanatory diagram showing the relationship between the cumulative driving time and the polarization processing execution period of the ultrasound transducer 48 and the reception sensitivity of the ultrasound transducer 48. The symbol S in the diagram indicates an execution period of diagnostic step, the symbol Q in the diagram indicates an execution period of standby step, and the symbol R in the diagram indicates an execution period of polarization processing.

The ultrasound transducer 48 is polarized up to a predetermined level at an initial time (for example, at the time of factory shipment), and can transmit and receive ultrasound waves with a reception sensitivity (hereinafter, initial sensitivity Pi) according to the degree of polarization. On the other hand, in a case where the ultrasound transducer 48 is driven to transmit and receive ultrasound waves for performing ultrasound diagnosis, depolarization progresses as the cumulative driving time increases, and the reception sensitivity also decreases accordingly. Such a tendency becomes noticeable in a case where the ultrasound transducer 48 is a single crystal transducer. Therefore, in a case where the cumulative driving time of the plurality of ultrasound transducers 48 for ultrasound diagnosis becomes equal to or longer than the specified time, it is necessary to generate a trigger and perform polarization processing.

Here, the cumulative driving time Ta of the ultrasound transducer (driving target transducer) 48 is expressed as the total time of required times (ta1, ta2, . . . , and tan in FIG. 9) for each ultrasound diagnosis. However, in a case where the cumulative driving time Ta exceeds the specified time, the reception sensitivity of the ultrasound transducer 48 falls below the lower limit sensitivity Pl, as shown in FIG. 9. The lower limit sensitivity Pl corresponds to the lower limit level of the sensitivity to be satisfied in maintaining the image quality of the ultrasound image. In other words, the specified time is set to a value corresponding to the lower limit sensitivity Pl.

The CPU 152 cannot directly detect whether or not the reception sensitivity of the ultrasound transducer 48 falls below the lower limit sensitivity Pl. Therefore, in a case where the cumulative driving time Ta exceeds the above-described specified time, the CPU 152 determines that the reception sensitivity falls below the lower limit sensitivity Pl.

Therefore, in the present embodiment, in a case where the cumulative driving time Ta becomes equal to or longer than the specified time, that is, in a case where the reception sensitivity of the ultrasound transducer 48 becomes equal to or less than the lower limit sensitivity Pl, the operation mode is shifted from the first mode to the second mode, and polarization processing is appropriately performed in the second mode. As a result, the depolarized ultrasound transducer 48 can be repolarized to restore the reception sensitivity of the ultrasound transducer 48.

Returning to the description of the diagnostic process, in a case where the operation mode is set to the second mode, ultrasound diagnosis and polarization processing are performed according to the steps shown in FIG. 7. Specifically, it is determined whether or not there is a diagnosis start instruction from the operator (S021). In a case where there is a diagnosis start instruction from the operator (Yes in S021), the CPU 152 controls each unit of the ultrasound processor apparatus 14 to perform a diagnostic step shown in FIG. 8 (S022). Thereafter, the process returns to step S007 in FIG. 5 to repeat the above-described operation.

In a case where there is no diagnosis start instruction from the operator in step S021 (No in S021), it is then determined whether or not this is a non-diagnosis period (S023). In a case where it is determined that this is not a non-diagnosis period (No in S023), the process returns to step S021 to repeat the operation described above.

In a case where it is determined that this is a non-diagnosis period in step S023 (Yes in S023), the CPU 152 performs polarization processing during the non-diagnosis period (S024). Specifically, in the polarization processing, a polarization voltage is supplied to the polarization target transducer for a predetermined time. In one polarization processing, all the N ultrasound transducers 48 are used as the polarization target transducers. More specifically, in one polarization processing, first, a polarization voltage is supplied to half (m) of the N ultrasound transducers 48, and then a polarization voltage is supplied to the remaining half (m) of the ultrasound transducers 48.

In the present embodiment, while the operation mode is the second mode, as shown in FIG. 9, polarization processing is repeatedly performed each time a non-diagnosis period comes.

After the execution of the polarization processing, the CPU 152 determines whether or not a difference (Tr−Ta) obtained by subtracting the cumulative driving time Ta of the plurality of ultrasound transducers 48 for performing ultrasound diagnosis from the cumulative processing time Tr of the plurality of ultrasound transducers 48 for performing polarization processing is equal to or greater than a threshold value (S025).

The cumulative processing time Tr is expressed as the total time of required times (tr1, tr2, ..., and trn in FIG. 9) for each polarization processing. The threshold value is set to an appropriate value for restoring the reception sensitivity of the ultrasound transducer 48 to the initial sensitivity Pi, and is recorded on the ultrasound processor apparatus 14 side.

The threshold value may be different for each ultrasound endoscope 12, or may be a value common to the ultrasound endoscopes 12. In addition, a default value may be set as the threshold value, or the operator may change the threshold value through the console 100.

From the cumulative driving time (transmission time) Ta, it can be seen how much the reception sensitivity of the ultrasound transducer 48 has decreased. In the example shown in FIG. 9, it can be calculated from ta1+ta2 to what extent the reception sensitivity of the ultrasound transducer 48 has decreased exceeding the lower limit sensitivity Pl. In addition, from the cumulative processing time (recovery time) Tr, it can be seen how much the reception sensitivity of the ultrasound transducer 48 is restored.

In the example shown in FIG. 9, assuming that the sensitivity reduction rate and the sensitivity recovery rate according to time are the same, ta1+ta2+ta3+ta4=tr1+tr2+tr3. In practice, sensitivity recovery is possible in a short time, and the sensitivity recovery rate is higher than the sensitivity reduction rate. Therefore, ta1+ta2+ta3+ta4=α (tr1+tr2+tr3) (α>1), and the relationship of Ta=αTr is satisfied.

For example, a threshold value can be determined based on the above-described relationship. Alternatively, a correspondence table showing the relationship between the cumulative driving time Ta and a threshold value required to restore the reception sensitivity of the ultrasound transducer 48, which has been lowered according to the cumulative driving time Ta, up to the initial sensitivity Pi can be created in advance, and a threshold value can be calculated and used from the cumulative driving time Ta using the correspondence table.

As a result, in the second mode, in a case where the difference obtained by subtracting the cumulative driving time Ta from the cumulative processing time Tr is less than the threshold value (No in S025), the process returns to step S021 to repeat the above-described operation.

On the other hand, in a case where the difference obtained by subtracting the cumulative driving time Ta from the cumulative processing time Tr is equal to or greater than the threshold value (Yes in S025), the CPU 152 accesses the endoscope side memory 58 and clears the cumulative driving time Ta stored in the endoscope side memory 58 so as to be rewritten to the initial value (zero) (S026). Step S026 in which the cumulative driving time Ta is cleared may be performed after the operation mode is returned from the second mode to the first mode in the next step S027.

Then, the CPU 152 returns the operation mode of the ultrasound diagnostic apparatus 10 from the second mode to the first mode (S027). Thereafter, the process returns to step S007 in FIG. 5 to repeat the above-described operation. That is, in the present embodiment, in a case where the difference obtained by subtracting the cumulative driving time Ta from the cumulative processing time Tr is equal to or greater than the threshold value in the second mode, the operation mode is shifted from the second mode to the first mode. This is because it is thought that the depolarized ultrasound transducer 48 is already sufficiently polarized at this time.

This will be specifically described below with reference to FIG. 9. In a case where the operation mode shifts to the second mode, polarization processing is performed during the non-diagnosis period as described above. As a result, as shown in FIG. 9, the polarization level and the reception sensitivity of each ultrasound transducer 48 are restored by an amount corresponding to the cumulative processing time Tr (tr1, tr2, and tr3 in FIG. 9) of the plurality of ultrasound transducers 48 for performing polarization processing. On the other hand, even while the operation mode is the second mode, ultrasound diagnosis is performed in a case where there is an instruction to start diagnosis. For this reason, even while the operation mode is the second mode, the cumulative driving time Ta of the plurality of ultrasound transducers 48 for performing ultrasound diagnosis increases by the time required for each ultrasound diagnosis (ta3 and ta4 in FIG. 9), and the polarization level and the reception sensitivity of each ultrasound transducer 48 decrease with an increase in the cumulative driving time Ta.

As described above, while the operation mode is the second mode, as shown in FIG. 9, the polarization of the ultrasound transducer 48 by polarization processing and the depolarization of the ultrasound transducer 48 by ultrasound diagnosis coexist. Then, in a case where the polarization processing and the ultrasound diagnosis are repeatedly performed, the cumulative processing time Tr (=tr1+tr2+tr3) becomes larger than the cumulative driving time Ta (=ta1+ta2+ta3+ta4) soon while the operation mode is the second mode, and finally, the difference (Tr−Ta) obtained by subtracting the cumulative driving time Ta from the cumulative processing time Tr becomes equal to or greater than the threshold value. At this point in time, as is apparent from FIG. 9, each ultrasound transducer 48 is polarized up to a level at which the reception sensitivity becomes the initial sensitivity Pi. In such a state, it is no longer necessary to perform the polarization processing. Therefore, in the present embodiment, the operation mode is returned from the second mode to the first mode in a case where the above-described conditions are satisfied.

Next, a specific example of the non-diagnosis period will be described.

For example, in a freeze mode in which an image (still image) of one frame of an ultrasound image (moving images) is displayed on the monitor 20, the CPU 152 can perform polarization processing. In the freeze mode, no ultrasound image is acquired. Since the freeze mode is a period other than the execution period of ultrasound diagnosis, that is, a non-diagnosis period during which transmission of ultrasound waves and reception of reflected waves for performing ultrasound diagnosis are not performed, it is possible to appropriately perform the polarization processing.

The CPU 152 can perform polarization processing in a case where a screen for setting control parameters of the ultrasound diagnostic apparatus, a screen for inputting information of a patient (patient's name, ID, and the like) to be subjected to ultrasound diagnosis, a screen for designating a part to be subjected to ultrasound diagnosis, and the like are displayed on the monitor 20. In a case where these screens are displayed, the user can input corresponding data. Accordingly, since this is a non-diagnosis period similarly, it is possible to appropriately perform the polarization processing.

In addition, the CPU 152 can perform polarization processing in a case where a screen, on which an ultrasound image generated (acquired) in the past and stored in the cine memory 150 is read out and displayed, is displayed on the monitor 20. In a case where the screen displaying an ultrasound image generated in the past is displayed, the user views the ultrasound image generated in the past. Therefore, since this is a non-diagnosis period similarly, it is possible to appropriately perform the polarization processing.

The ultrasound diagnostic apparatus 10 can acquire an ultrasound image and an endoscope image and display the ultrasound image and the endoscope image on the monitor 20 in various display modes.

As shown in FIG. 10, the display modes include a first display mode in which only an ultrasound image is displayed, a second display mode in which an ultrasound image is displayed so as to be larger than an endoscope image by using picture in picture (PinP), a third display mode in which an ultrasound image is displayed so as to be smaller than an endoscope image by using the PinP similarly, and a fourth display mode in which only an endoscope image is displayed. The first to fourth display modes can be freely switched and displayed according to the user's instruction.

In the fourth display mode, that is, in a case where only the endoscope image is displayed on the monitor 20, the CPU 152 can perform polarization processing. In the fourth display mode, no ultrasound image is acquired. Accordingly, since this is a non-diagnosis period similarly, it is possible to appropriately perform the polarization processing.

In addition, the CPU 152 can perform polarization processing in the third display mode, that is, in a case where the ultrasound image is displayed on the monitor 20 so as to be smaller than the endoscope image by picture in picture. In the third display mode, ultrasound diagnosis is actually performed, and this is not a non-diagnosis period but the ultrasound image is displayed so as to be smaller than the endoscope image. Therefore, it is possible to appropriately perform the polarization processing regardless of the image quality.

In this case, the CPU 152 controls the notification circuit 156 to notify the user that the polarization processing is being performed. In response to this, the notification circuit 156 notifies the user that the polarization processing is being performed. That is, in the third display mode, the user can know that the polarization processing is being performed. Thereafter, the CPU 152 sets the freeze mode, that is, forcibly sets the non-diagnosis period and performs polarization processing.

Although the specific examples of the non-diagnosis period have been described above, the polarization processing may be performed in any non-diagnosis period other than in the specific examples described above.

Next, a pulse waveform and a driving waveform (transmission waveform) of a polarization driving pulse (transmission wave for polarization) of the second transmission signal transmitted from the transmission circuit 144 to the ultrasound transducer 48 in the invention will be described.

Figure 11A:
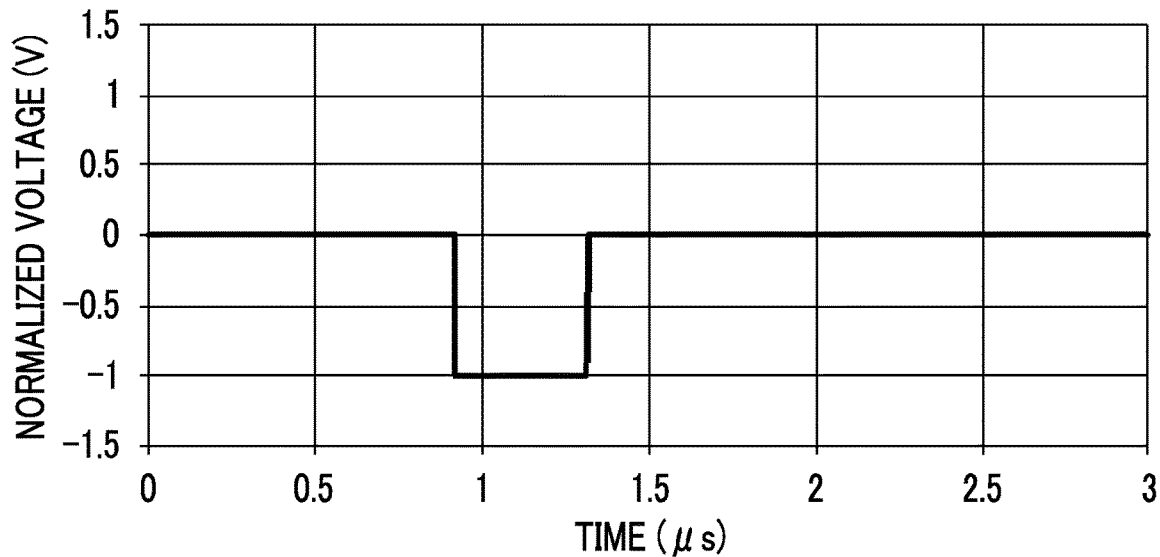
FIG. 11A is a graph showing an example of a driving waveform of a polarization driving pulse transmitted from a transmission circuit shown in FIG. 4.
Figure 11B:
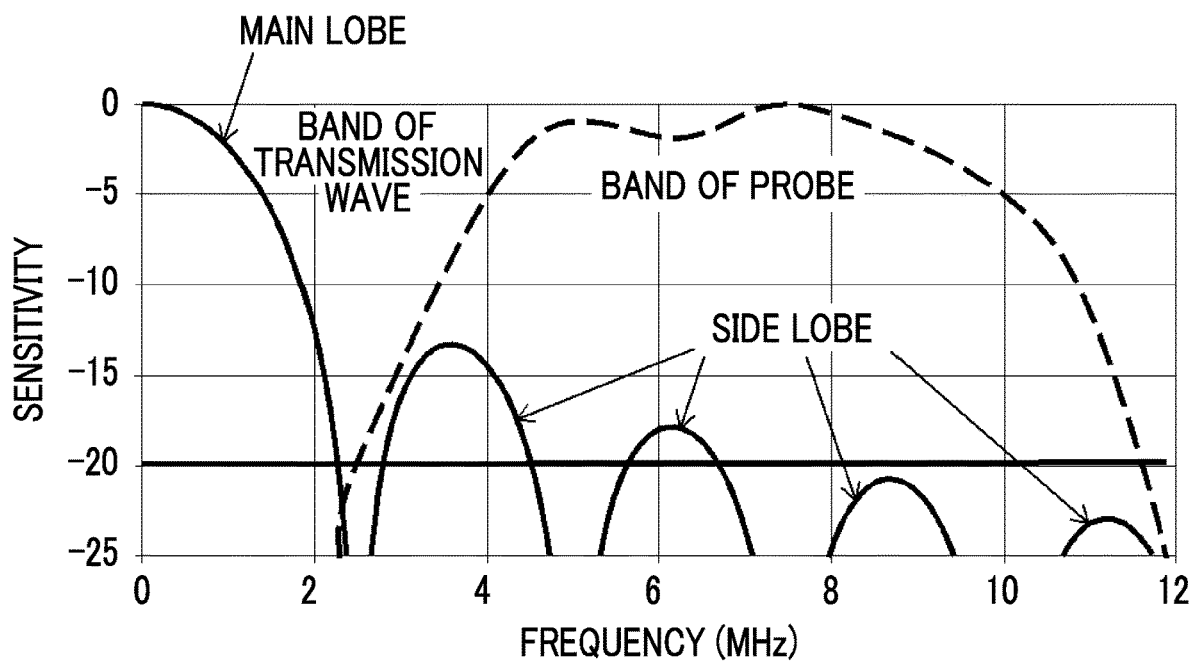
FIG. 11B is a graph showing the relationship between the frequency and the sensitivity of the driving waveform of the polarization driving pulse shown in FIG. 11A.

FIGS. 11A and 11B are graphs of an example of a driving waveform of a polarization driving pulse transmitted from the transmission circuit shown in FIG. 4, and are graphs showing the relationship between the sensitivity and the frequency of the driving waveform. The driving waveform shown in FIG. 11A is a waveform of one unipolar wave having a frequency of 1.25 MHz.

In the invention, the driving waveform of the polarization driving pulse is not particularly limited but has a unipolar waveform shown in FIG. 11A, and it is preferable to perform polarization processing of the ultrasound transducer 48 using a polarization driving pulse having a driving waveform having a frequency characteristic shown by the solid line in FIG. 11B. In the example shown in FIG. 11B, for example, at a sensitivity level of −20 dB or more, the probe frequency band for acquiring an ultrasound image is about 2.7 MHz to about 11.7 MHz as shown by the broken line, while the band of the main lobe of the driving waveform of the polarization driving pulse shown by the solid line is about 2.3 MHz or less. That is, the band characteristic of the frequency of the polarization driving pulse and the band characteristic of the frequency of the diagnostic driving pulse do not overlap each other at a sensitivity level of −20 dB or more.

That is, in the invention, as shown in FIG. 11B, in the driving waveform of the polarization driving pulse, it is preferable that the frequency band of the main lobe and the probe frequency band shown by the broken line do not overlap each other at a sensitivity level of −20 dB or more. In addition, it is preferable that the frequency band of the main lobe is lower than the probe frequency band at a sensitivity level of −20 dB or more. The reason is that, in the polarization processing, it is necessary to reduce an influence on the ultrasound image by preventing excessive ultrasound wave output and to reduce an influence on the body cavity of the subject due to temperature rise by preventing the temperature rise. In particular, the upper limit temperature of the distal end portion of the ultrasound endoscope 12 inserted into the body cavity of the subject is strictly limited so as not to affect the body cavity and the like, and it is necessary to prevent the temperature rise.

In the invention, since the polarization driving pulse (main lobe) is transmitted outside the probe frequency band, the energy input to the ultrasound transducer 48 is reduced. Therefore, the temperature rise can be suppressed. In addition, since the outside of the probe frequency band is the outside of a resonance band in which the ultrasound transducer 48 resonates. Accordingly, the output sound pressure is reduced even though the polarization driving pulse (main lobe) is applied to the ultrasound transducer 48.

In the driving waveform of the polarization driving pulse shown in FIG. 11B, it can be seen that, in addition to the main lobe, within the probe frequency band, one or more side lobes similarly shown by the solid line (in the example shown in FIG. 11B, four side lobes) are generated. As shown in FIG. 11B, it is preferable that all the maximum sensitivities of the side lobes within the probe frequency band are equal to or less than −10 dB and the average sensitivity of the side lobes is equal to or less than −20 dB. The reason is as follows.

In general, the specification of the frequency characteristic of the probe is expressed in the −20 dB band of the transmission and reception sensitivity. This is because the signal of 1/10 or less from the peak of the sensitivity hardly affects an image. On the other hand, the band of the transmission wave is different from that in the case of the probe. Since only a transmission portion is taken into consideration, the level of 20 dB/2=10 dB is the threshold value. For this reason, −10 dB is more preferable in a case where a transmission component is considered.

Figure 12A:
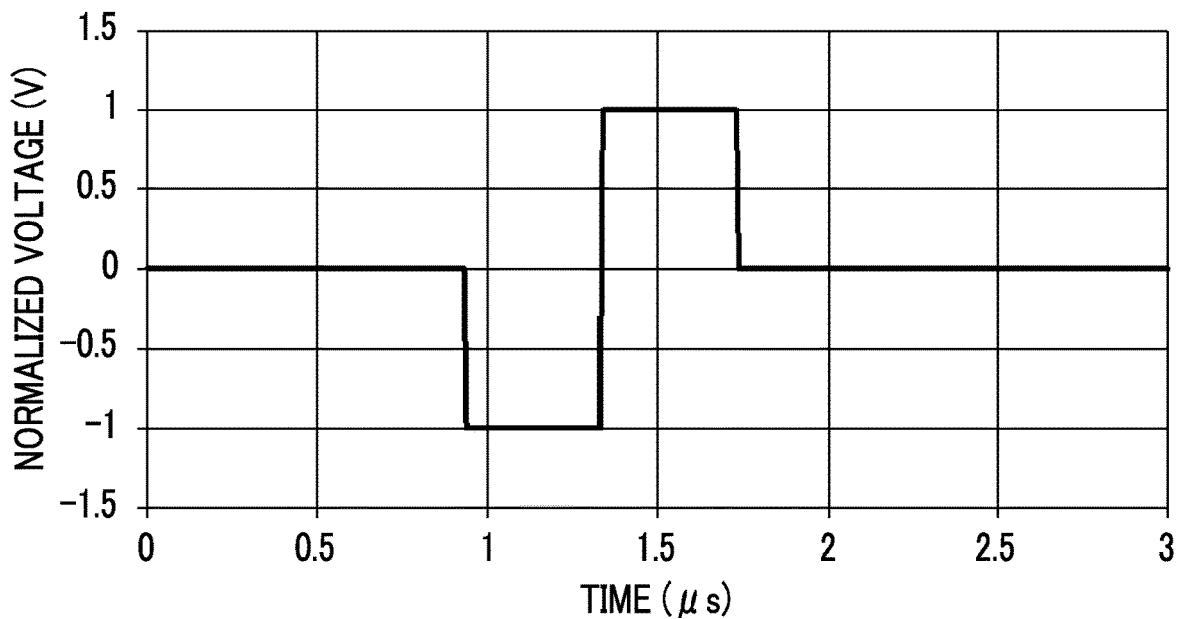
FIG. 12A is a graph showing another example of the driving waveform of the polarization driving pulse transmitted from the transmission circuit shown in FIG. 4.
Figure 12B:
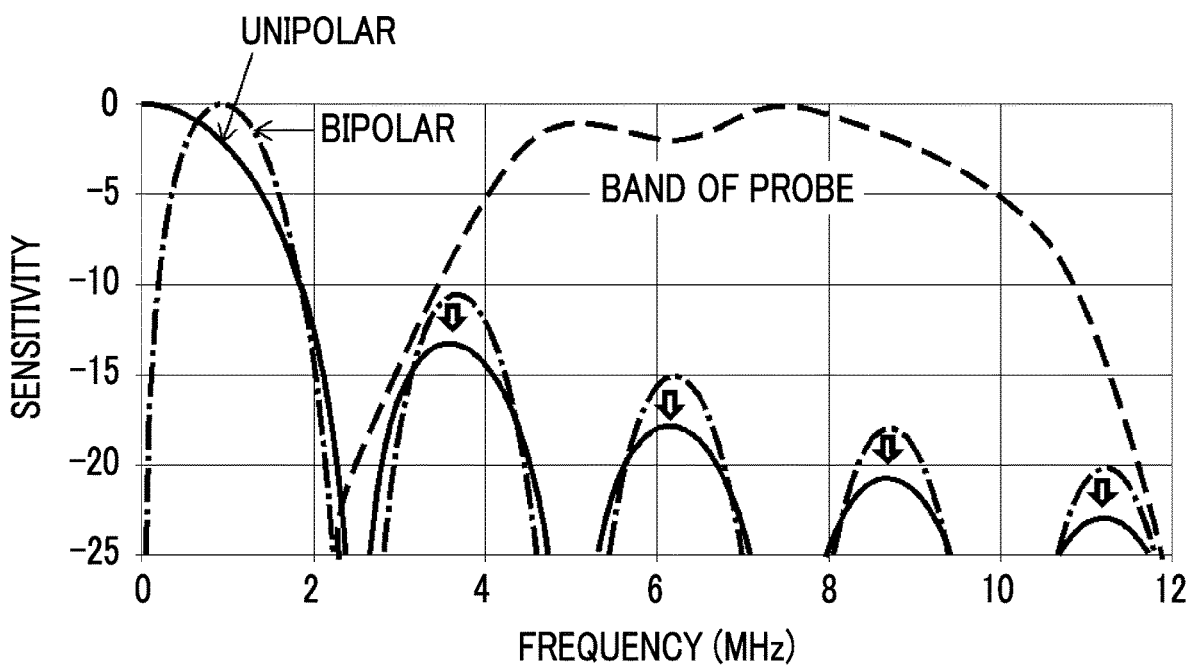
FIG. 12B is a graph showing the relationship between the frequency and the sensitivity of the driving waveform of the polarization driving pulse shown in FIG. 11A and the relationship between the frequency and the sensitivity of the driving waveform of the polarization driving pulse shown in FIG. 12A.

In the invention, the driving waveform of the polarization driving pulse is not particularly limited, and may be a bipolar waveform shown in FIG. 12A. However, the driving waveform of the polarization driving pulse is preferably a unipolar waveform as shown in FIG. 11A. The reason is that, as in the frequency characteristic of the driving waveform shown in FIG. 12B, the sensitivity of the main lobe does not change whether the driving waveform is a unipolar waveform shown by the solid line or a bipolar waveform shown by the one-dot chain line, but the sensitivities of all of the four side lobes in the case of the unipolar waveform are lower than those in the case of the bipolar waveform.

Therefore, by forming the transmission waveform as a unipolar waveform as shown in FIG. 11A, not only the main lobe but harmonic components can be suppressed. As a result, higher effects can be expected.

Figure 13A:
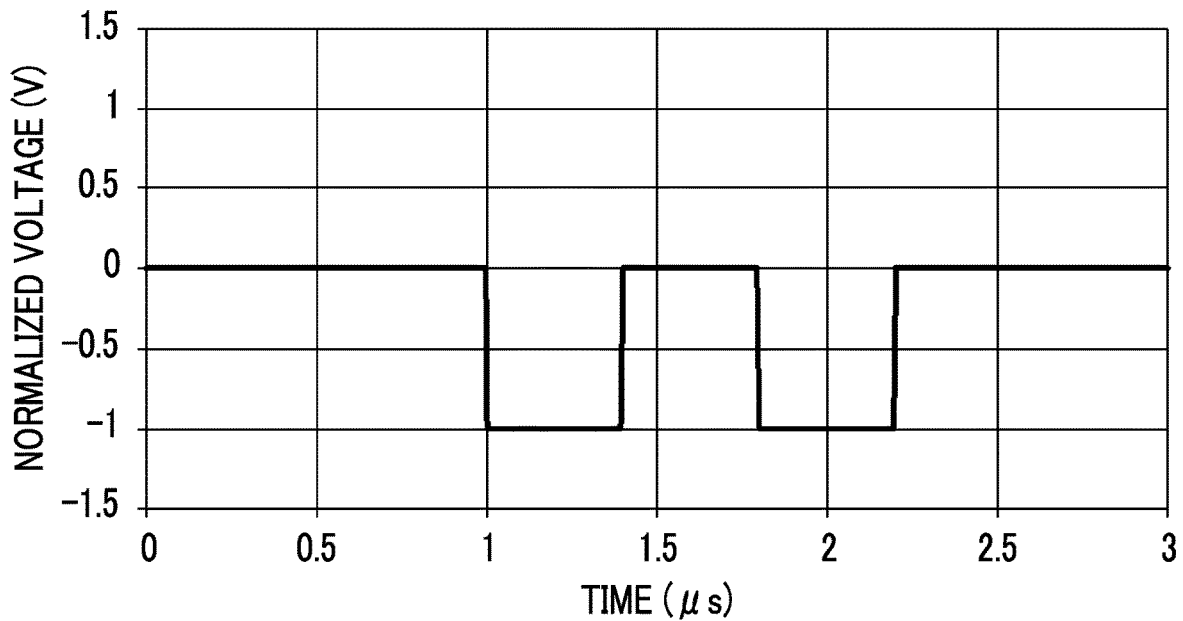
FIG. 13A is a graph showing another example of the pulse waveform of the polarization driving pulse transmitted from the transmission circuit shown in FIG. 4.
Figure 13B:
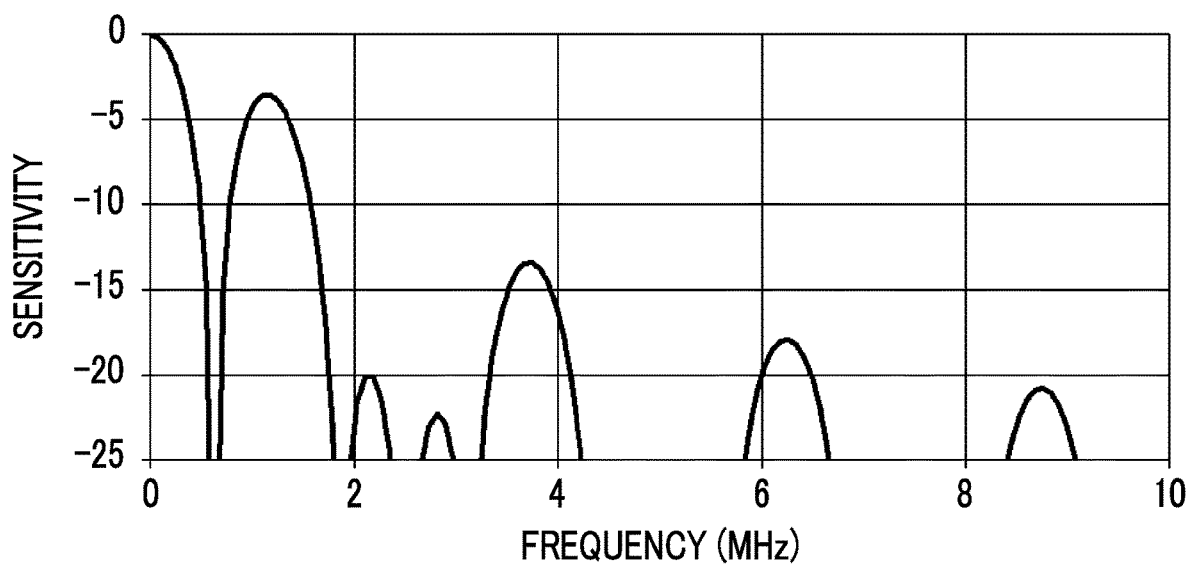
FIG. 13B is a graph showing the relationship between the frequency and the sensitivity of the driving waveform of the polarization driving pulse shown in FIG. 13A.

As shown in FIG. 13A, a plurality of unipolar waveforms may be transmitted as the polarization driving pulses. In the example shown in FIG. 13A, two pulse waves may be transmitted. The polarization driving pulse shown in FIG. 13A has a driving waveform including two pulse waves as a driving waveform of the polarization driving pulse shown in FIG. 11A. The frequency characteristic of the driving waveform of the polarization driving pulse shown in FIG. 13A is shown in FIG. 13B. The frequency characteristic of the driving waveform shown in FIG. 13B is different from the frequency characteristic of the driving waveform shown in FIG. 11B in terms of the waveform of the main lobe, but the waveform of the side lobe does not change much.

Figure 13C:
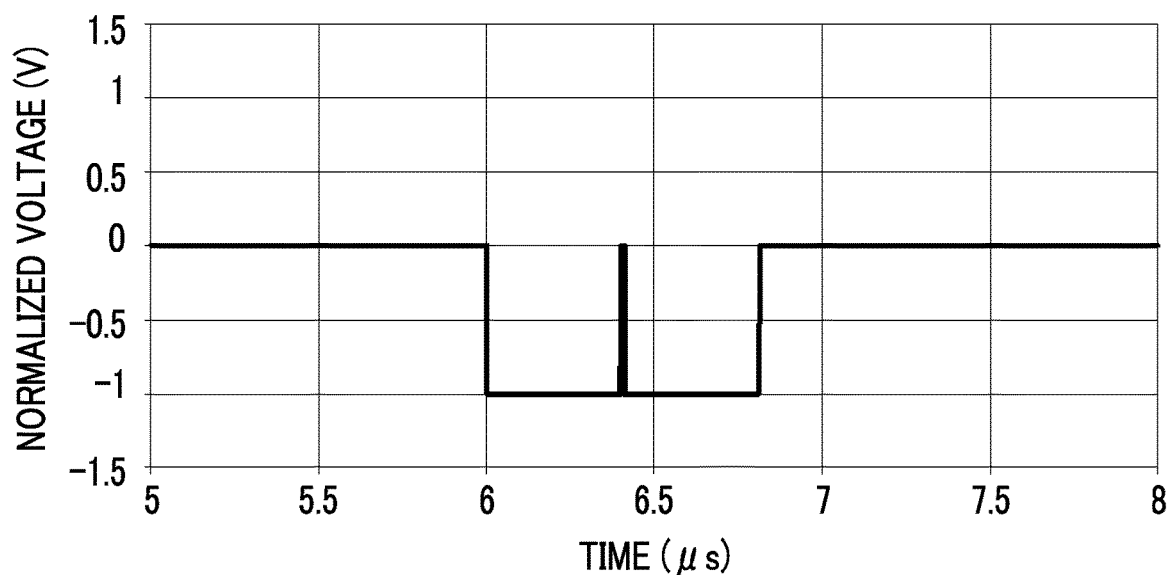
FIG. 13C is a graph showing another example of the pulse waveform of the polarization driving pulse transmitted from the transmission circuit shown in FIG. 4.

In addition, as shown in FIG. 13C, it is preferable to transmit a polarization driving pulse in which a plurality of pulse waveforms are connected to each other with the time of the minimum number of clocks between driving waveforms of the polarization driving pulse as unipolar waveforms. That is, in the invention, it is preferable that the transmission circuit 144 outputs a plurality of unipolar waveforms as polarization driving pulses with the time of the minimum number of clocks defined in the ultrasound processor apparatus 14 as an interval between the unipolar waveforms.

The reason is that it is optimal to apply a DC voltage for polarization processing, but the DC voltage cannot be transmitted in a case where the transmission circuit 144 having an existing transmission circuit configuration is used as in the invention.

The minimum and maximum time widths are determined depending on the type of pulser (pulse generation circuit 158) of the transmission circuit 144 of the ultrasound processor apparatus 14 used in the ultrasound diagnostic apparatus 10. Therefore, by using the time of the minimum number of clocks defined in the transmission circuit 144 as the minimum time width, a high repolarization effect can be expected by putting the minimum time width between a plurality of unipolar waveforms so that a polarization processing waveform close to a DC voltage is obtained. The minimum time width between two unipolar pulse waveforms, that is, the minimum pulse width is determined by the specification of the pulser (pulse generation circuit 158) of the transmission circuit 144. Control to comply with this specification is provided from the above-described FPGA in the transmission circuit 144.

Figure 13D:
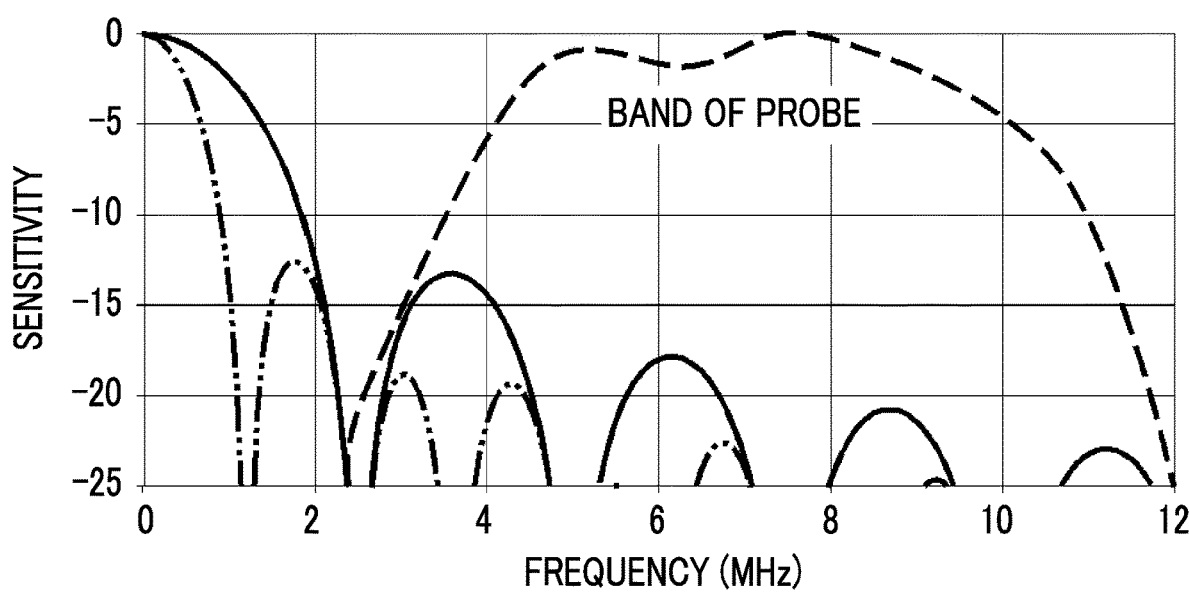
FIG. 13D is a graph showing the relationship between the frequency and the sensitivity of the driving waveform of the polarization driving pulse shown in FIG. 13C.

As shown by a two-dot chain line in FIG. 13D, by using a combination of a plurality of unipolar waveforms shown in FIG. 13C as the driving waveform of the polarization driving pulse, it is possible to reduce the maximum sensitivity of the side lobe more than in the case of the driving waveform of the polarization driving pulse including one unipolar waveform shown by the solid line in FIG. 13D.

Figure 14A:
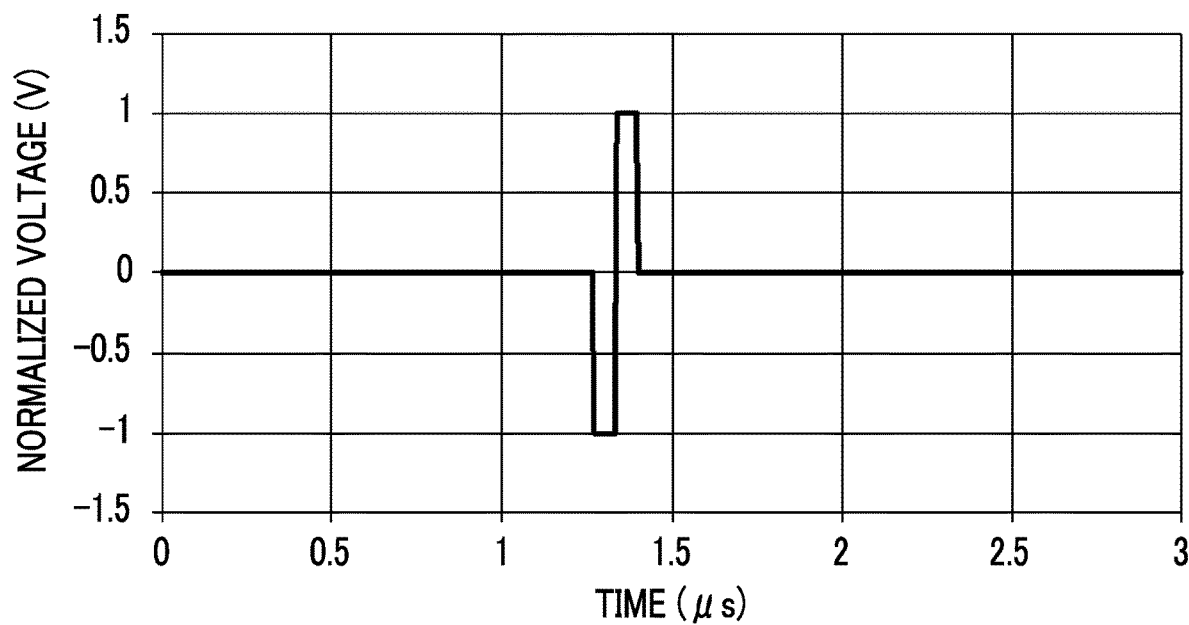
FIG. 14A is a graph showing another example of the pulse waveform of the diagnostic driving pulse transmitted from the transmission circuit shown in FIG. 4.
Figure 14B:
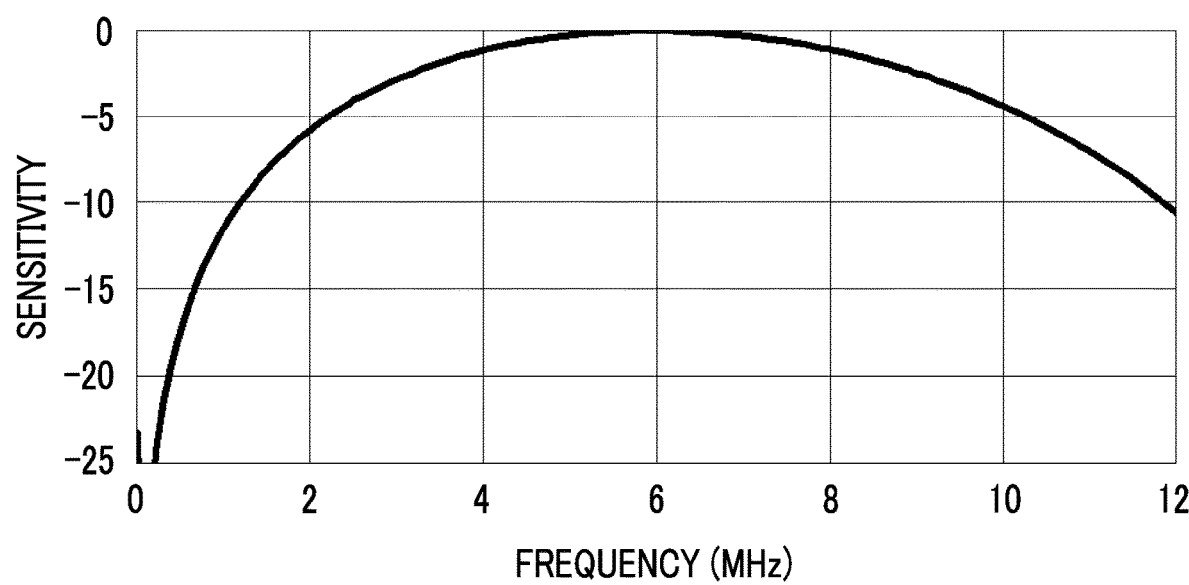
FIG. 14B is a graph showing the relationship between the frequency and the sensitivity of the driving waveform of the diagnostic driving pulse shown in FIG. 14A.

On the other hand, FIGS. 14A and 14B are graphs of an example of a driving waveform of a diagnostic driving pulse transmitted from the transmission circuit shown in FIG. 4, and are graphs showing the relationship between the sensitivity and the frequency of the driving waveform. The driving waveform shown in FIG. 14A is a waveform of one bipolar wave having a center frequency of 6 MHz. The frequency characteristic of the driving waveform of the diagnostic driving pulse is shown in FIG. 14B.

<<Effectiveness of Ultrasound Diagnostic Apparatus 10 of the Invention>>

The ultrasound diagnostic apparatus 10 performs polarization processing using the existing transmission circuit 144, more specifically, the pulse generation circuit 158. In the ultrasound diagnostic apparatus 10, the second transmission signal in the case of performing polarization processing is a pulse wave, and the pulse generation circuit 158 does not need to output a DC waveform. Therefore, it is possible to perform the polarization processing without significantly changing the existing circuit and accordingly without increasing the cost.

In addition, since the polarization processing is performed during the non-diagnosis period, the frame rate is not reduced. Therefore, without reducing the image quality of the ultrasound image, the reception sensitivities of the plurality of ultrasound transducers 48 can always be kept satisfactory. As a result, a high-quality ultrasound image can always be acquired.

The total number of ultrasound transducers 48 and the number of opening channels may be changed to any number. For example, in a case where the number of opening channels is the same as the total number of ultrasound transducers 48, the 128 ultrasound transducers 48 can be simultaneously subjected to polarization processing instead of performing the polarization processing in two steps. Alternatively, in a case where the number of opening channels is ¼ of the total number of ultrasound transducers 48, the 32 ultrasound transducers 48 can be simultaneously subjected to polarization processing in each of four steps. The characteristics of the above respective embodiments may be implemented in combination.

While the invention has been described in detail, the invention is not limited to the above-described embodiment, and various improvements and modifications may be made without departing from the scope and spirit of the invention.

EXPLANATION OF REFERENCES

10: ultrasound diagnostic apparatus
12: ultrasound endoscope
14: ultrasound processor apparatus
16: endoscope processor apparatus
18: light source device
20: monitor
21*a*: water supply tank
21*b*: suction pump
22: insertion part
24: operation unit
26: universal cord
28*a*: air and water supply button
28*b*: suction button
29: angle knob
30: treatment tool insertion port
32*a*: ultrasound connector
32*b*: endoscope connector
32*c*: light source connector
34*a*: air and water supply tube
34*b*: suction tube
36: ultrasound observation portion
38: endoscope observation portion
40: distal end portion
42: bending portion
43: flexible portion 44: treatment tool lead-out port
45: treatment tool channel
46: ultrasound transducer unit
48: ultrasound transducer
50: ultrasound transducer array
54: backing material layer
56: coaxial cable
58: endoscope side memory
60: FPC
74: acoustic matching layer
76: acoustic lens
82: observation window
84: objective lens
86: solid-state imaging element
88: illumination window
90: cleaning nozzle
92: wiring cable
100: console
140: multiplexer
142: reception circuit
144: transmission circuit
146: A/D converter
148: ASIC
150: cine memory
151: memory controller
152: CPU
154: DSC
156: notification circuit
158: pulse generation circuit
160: phase matching unit
162: B mode image generation unit
164: PW mode image generation unit
166: CF mode image generation unit

What is claimed is:

1. An ultrasound diagnostic apparatus acquiring an ultrasound image and an endoscope image, comprising:
    an ultrasound endoscope comprising an ultrasound observation portion that transmits ultrasound waves using an ultrasound transducer array in which a plurality of ultrasound transducers are arranged, receives reflected waves of the ultrasound waves, and outputs a reception signal; and
    an ultrasound processor apparatus that generates the ultrasound image by converting the reception signal into an image,
    wherein the ultrasound processor apparatus comprises:
    a control circuit that alternately performs ultrasonic diagnosis and polarization process until a difference obtained by subtracting a cumulative driving time from a cumulative processing time of the plurality of ultrasound transducers for performing the polarization processing becomes equal to or greater than a threshold value, in a case where the cumulative driving time of the plurality of ultrasound transducers for performing ultrasound diagnosis becomes equal to or longer than a specified time, the control circuit performing the polarization processing on the plurality of ultrasound transducers in a non-diagnosis period, during which transmission of the ultrasound waves and reception of the reflected waves for performing the ultrasound diagnosis are not performed; and
    a transmission circuit with a pulse generation circuit that generates a transmission signal for driving the plurality of ultrasound transducers to generate the ultrasound waves using the pulse generation circuit and supplies the transmission signal to the plurality of ultrasound transducers under control of the control circuit, wherein
    the transmission circuit generates a first transmission signal having a driving voltage for performing the ultrasound diagnosis using the pulse generation circuit in a case of performing the ultrasound diagnosis, and generates a second transmission signal having a polarization voltage for performing the polarization processing using the same pulse generation circuit as in the case of generating the first transmission signal in a case of performing the polarization processing, and
    reception signals of the plurality of ultrasound transducers in a frequency band of a first ultrasound wave generated by the first transmission signal and reception signals of the plurality of ultrasound transducers in a frequency band of a main lobe of a second ultrasound wave generated by the second transmission signal have different band characteristics.

2. The ultrasound diagnostic apparatus according to claim 1,
    wherein band characteristics of the reception signals of the plurality of ultrasound transducers in the frequency band of the first ultrasound wave generated by the first transmission signal and band characteristics of the reception signals of the plurality of ultrasound transducers in the frequency band of the main lobe of the second ultrasound wave generated by the second transmission signal do not overlap at a level of −20 dB or more.

3. The ultrasound diagnostic apparatus according to claim 2,
    wherein an operation mode includes a first mode in which the polarization processing is not performed during the non-diagnosis period and a second mode in which the polarization processing is performed during the non-diagnosis period, and
    the control circuit shifts the operation mode from the first mode to the second mode in a case where the cumulative driving time becomes equal to or longer than the specified time in the first mode, and shifts the operation mode from the second mode to the first mode in a case where a difference obtained by subtracting the cumulative driving time from a cumulative processing time of the plurality of ultrasound transducers for performing the polarization processing becomes equal to or greater than a threshold value in the second mode.

4. The ultrasound diagnostic apparatus according to claim 3,
    wherein the control circuit performs the polarization processing in a case of a freeze mode in which an image of one frame of the ultrasound image is displayed.

5. The ultrasound diagnostic apparatus according to claim 3,
    wherein the control circuit performs the polarization processing in a case where a screen for setting a control parameter of the ultrasound diagnostic apparatus is displayed.

6. The ultrasound diagnostic apparatus according to claim 2,
    wherein the control circuit performs the polarization processing in a case of a freeze mode in which an image of one frame of the ultrasound image is displayed.

7. The ultrasound diagnostic apparatus according to claim 2,
    wherein the control circuit performs the polarization processing in a case where a screen for setting a control parameter of the ultrasound diagnostic apparatus is displayed.

8. The ultrasound diagnostic apparatus according to claim 1,
wherein an operation mode includes a first mode in which the polarization processing is not performed during the non-diagnosis period and a second mode in which the polarization processing is performed during the non-diagnosis period, and
the control circuit shifts the operation mode from the first mode to the second mode in a case where the cumulative driving time becomes equal to or longer than the specified time in the first mode, and shifts the operation mode from the second mode to the first mode in a case where a difference obtained by subtracting the cumulative driving time from a cumulative processing time of the plurality of ultrasound transducers for performing the polarization processing becomes equal to or greater than a threshold value in the second mode.

9. The ultrasound diagnostic apparatus according to claim 8,
wherein the control circuit performs the polarization processing in a case of a freeze mode in which an image of one frame of the ultrasound image is displayed.

10. The ultrasound diagnostic apparatus according to claim 8,
wherein the control circuit performs the polarization processing in a case where a screen for setting a control parameter of the ultrasound diagnostic apparatus is displayed.

11. The ultrasound diagnostic apparatus according to claim 1,
wherein the control circuit performs the polarization processing in a case of a freeze mode in which an image of one frame of the ultrasound image is displayed.

12. The ultrasound diagnostic apparatus according to claim 1,
wherein the control circuit performs the polarization processing in a case where a screen for setting a control parameter of the ultrasound diagnostic apparatus is displayed.

13. The ultrasound diagnostic apparatus according to claim 1,
wherein the control circuit performs the polarization processing in a case where a screen for inputting information of a patient to be subjected to the ultrasound diagnosis is displayed.

14. The ultrasound diagnostic apparatus according to claim 1,
wherein the control circuit performs the polarization processing in a case where a screen for designating a part to be subjected to the ultrasound diagnosis is displayed.

15. The ultrasound diagnostic apparatus according to claim 1,
wherein the control circuit performs the polarization processing in a case where a screen for displaying an ultrasound image generated in a past is displayed.

16. The ultrasound diagnostic apparatus according to claim 1,
wherein the control circuit performs the polarization processing in a case where only the endoscope image is displayed.

17. The ultrasound diagnostic apparatus according to claim 1,
wherein the ultrasound processor apparatus further comprises a notification circuit that notifies a user that the polarization processing is being performed, and
the control circuit controls the notification circuit to notify the user that the polarization processing is being performed in a case where the ultrasound image is displayed so as to be smaller than the endoscope image by picture in picture, and sets an operation mode to a freeze mode in which an image of one frame of the ultrasound image is displayed to perform the polarization processing.

18. An operation method of the ultrasound diagnostic apparatus according to claim 1 acquiring the ultrasound image and the endoscope image, comprising:
a step in which the ultrasound observation portion that the ultrasound endoscope of the ultrasound diagnostic apparatus comprises transmits ultrasound waves using the ultrasound transducer array in which the plurality of ultrasound transducers are arranged, receives the reflected waves of the ultrasound waves, and outputs the reception signal; and
a step in which the ultrasound processor apparatus of the ultrasound diagnostic apparatus generates the ultrasound image by converting the reception signal into an image,
wherein the step of generating the ultrasound image includes:
a step in which the control circuit of the ultrasound processor apparatus alternately performs the ultrasonic diagnosis and the polarization process until the difference obtained by subtracting the cumulative driving time from the cumulative processing time of the plurality of ultrasound transducers for performing the polarization processing becomes equal to or greater than the threshold value, in a case where the cumulative driving time of the plurality of ultrasound transducers for performing the ultrasound diagnosis becomes equal to or longer than the specified time, the control circuit performing the polarization processing on the plurality of ultrasound transducers in the non-diagnosis period, during which the transmission of the ultrasound waves and the reception of the reflected waves for performing the ultrasound diagnosis are not performed; and
a step in which the transmission circuit of the ultrasound processor apparatus generates the transmission signal for driving the plurality of ultrasound transducers to generate the ultrasound waves using the pulse generation circuit and supplies the transmission signal to the plurality of ultrasound transducers under control of the control circuit, the transmission circuit having the pulse generation circuit, the step of generating the transmission signal includes:
a step of generating the first transmission signal having the driving voltage for performing the ultrasound diagnosis using the pulse generation circuit in a case of performing the ultrasound diagnosis; and
a step of generating the second transmission signal having the polarization voltage for performing the polarization processing using the same pulse generation circuit as in the case of generating the first transmission signal in a case of performing the polarization processing, wherein
the reception signals of the plurality of ultrasound transducers in the frequency band of the first ultrasound wave generated by the first transmission signal and the reception signals of the plurality of ultrasound transducers in the frequency band of the main lobe of the second ultrasound wave generated by the second transmission signal have the different band characteristics.

19. The operation method of an ultrasound diagnostic apparatus according to claim 18, wherein band characteristics of the reception signals of the plurality of ultrasound transducers in the frequency band of the first ultrasound wave generated by the first transmission signal and band characteristics of the reception signals of the plurality of ultrasound transducers in the frequency band of the main lobe of the second ultrasound wave generated by the second transmission signal do not overlap at a level of −20 dB or more.

20. The operation method of an ultrasound diagnostic apparatus according to claim 18,
wherein an operation mode includes a first mode in which the polarization processing is not performed during the non-diagnosis period and a second mode in which the polarization processing is performed during the non-diagnosis period, and in the step of performing the polarization processing, the operation mode is shifted from the first mode to the second mode in a case where the cumulative driving time becomes equal to or longer than the specified time in the first mode, and the operation mode is shifted from the second mode to the first mode in a case where a difference obtained by subtracting the cumulative driving time from a cumulative processing time of the plurality of ultrasound transducers for performing the polarization processing becomes equal to or greater than a threshold value in the second mode.

\* \* \* \* \*